(12) United States Patent
Ishida

(10) Patent No.: US 11,331,207 B2
(45) Date of Patent: May 17, 2022

(54) STENT

(71) Applicant: Biomedical Solutions Inc., Tokyo (JP)

(72) Inventor: Hiroki Ishida, Tokyo (JP)

(73) Assignee: BIOMEDICAL SOLUTIONS INC., Tokyo (JP)

(*) Notice: Subject to any disclaimer, the term of this patent is extended or adjusted under 35 U.S.C. 154(b) by 0 days.

(21) Appl. No.: 17/094,582

(22) Filed: Nov. 10, 2020

(65) Prior Publication Data

US 2021/0145618 A1 May 20, 2021

(30) Foreign Application Priority Data

Nov. 15, 2019 (JP) .............................. JP2019-207421

(51) Int. Cl.
*A61F 2/82* (2013.01)
*A61F 2/915* (2013.01)
*A61F 2/95* (2013.01)

(52) U.S. Cl.
CPC ................ *A61F 2/82* (2013.01); *A61F 2/915* (2013.01); *A61F 2002/91583* (2013.01); *A61F 2002/9505* (2013.01); *A61F 2210/0057* (2013.01); *A61F 2220/0025* (2013.01); *A61F 2230/0043* (2013.01); *A61F 2250/0025* (2013.01);
(Continued)

(58) Field of Classification Search
CPC ...... A61F 2250/0096–0098; A61F 2230/0043; A61F 2220/0025; A61F 2/07–2002/007; A61F 2/24–2493; A61F 2/82–945
See application file for complete search history.

(56) References Cited

U.S. PATENT DOCUMENTS

| | | | |
|---|---|---|---|
| 2006/0173529 A1 | 8/2006 | Blank | |
| 2012/0259404 A1* | 10/2012 | Tieu | D04C 1/06 623/1.15 |
| 2018/0344337 A1 | 12/2018 | Losordo et al. | |

(Continued)

FOREIGN PATENT DOCUMENTS

| EP | 2777639 A1 | 9/2014 |
|---|---|---|
| WO | WO 2017/200956 A1 | 11/2017 |

OTHER PUBLICATIONS

"Stent", Free Online Medical Dictionary, pp. 1-3, accessed Jul. 10, 2013. (Year: 2013).*

(Continued)

*Primary Examiner* — Rebecca S Preston
(74) *Attorney, Agent, or Firm* — Muncy, Geissler, Olds & Lowe, P.C.

(57) ABSTRACT

A stent according to the invention includes: a strut extending in a predetermined direction; a first protrusion provided on the strut, the first protrusion being substantially L-shaped and extending in a direction away from the strut and in a direction toward a distal side in the predetermined direction; a second protrusion that is provided on the strut and located distal to the first protrusion, the second protrusion being substantially L-shaped, extending in a direction away from the strut and in a direction toward a proximal side in the predetermined direction, and having a tip spaced apart from a tip of the first protrusion; and an opaque member being substantially tubular and highly opaque to radiation, the opaque member having two end portions in which the first and second protrusions are inserted, respectively.

7 Claims, 20 Drawing Sheets

(52) U.S. Cl.
CPC ............... *A61F 2250/0039* (2013.01); *A61F 2250/0098* (2013.01)

(56) References Cited

U.S. PATENT DOCUMENTS

| | | | |
|---|---|---|---|
| 2019/0201218 A1 | 7/2019 | Shobayashi | |
| 2020/0155732 A1* | 5/2020 | Rangwala | ................. A61F 2/06 |
| 2020/0390515 A1* | 12/2020 | Lorenzo | ............... A61B 17/221 |

OTHER PUBLICATIONS

Extended European Search Report issued in the EP Patent Application No. 20206784.9, dated Apr. 15, 2021.

* cited by examiner

STENT

This application is based on and claims the benefit of priority from Japanese Patent Application No. 2019-207421, filed on 15 Nov. 2019, the content of which is incorporated herein by reference.

BACKGROUND OF THE INVENTION

Field of the Invention

The present invention relates to a stent that can be placed in a luminal structure of a living body to expand the lumen and then removed from the luminal structure.

Related Art

To treat stenosis of a luminal organ that has a luminal structure such as a blood vessel, a trachea, or a bowel, a flexible, cylindrical mesh stent can be used to expand the stenosed lumen so that the patency of the lesion site can be ensured. Such a stent is expanded (deployed) in the luminal structure to expand the luminal structure.

An opaque member (what is called a marker) that is highly opaque to radiation such as X-rays can also be provided on a strut of a stent (see, for example, Patent Document 1 listed below) to identify the position of the stent placed in a luminal structure. Such a stent can have improved clinical performance since the opaque member in the stent is rendered visible by radiation irradiation.

Patent Document 1: US Patent Application, Publication No. 2018/0344337

SUMMARY OF THE INVENTION

Such a stent needs to have high reliability to prevent the opaque member from coming off in a luminal structure. In the manufacture of such a stent, a high level of ease of attachment is also desired for the attachment of the opaque member to the strut.

It is an object of the present invention to provide a stent that has high reliability to prevent an opaque member from coming off in a luminal structure and includes a strut and an opaque member attached to the strut with a high level of ease of attachment.

An aspect of the present invention relates to a stent including: a strut extending in a predetermined direction; a first protrusion provided on the strut, the first protrusion being substantially L-shaped and extending in a direction away from the strut and in a direction toward a distal side in the predetermined direction; a second protrusion that is provided on the strut and located distal to the first protrusion, the second protrusion being substantially L-shaped, extending in a direction away from the strut and in a direction toward a proximal side in the predetermined direction, and having a tip spaced apart from a tip of the first protrusion; and an opaque member being substantially tubular and highly opaque to radiation, the opaque member having two end portions in which the first and second protrusions are inserted, respectively.

A distance of 30 µm to 10 mm may be provided between the tip of the first protrusion and the tip of the second protrusion.

The opaque member being substantially tubular may be stretchable in a tube axis direction.

The first protrusion may have a portion that extends in the predetermined direction and is longer than a portion of the second protrusion extending in the predetermined direction.

The first and second protrusions may each have a tip portion with an inclined shape on a side facing the strut.

The first and second protrusions may each have a convex-shaped portion that is opposite to the strut and at a base end of a portion extending in the predetermined direction.

The first and second protrusions may have portions that extend in the predetermined direction and are configured to be placed along a direction in which the stent is inserted into a catheter in a process of inserting the stent into the catheter, and configured to be placed inside the strut in a radial direction of the catheter in the process of inserting the stent into the catheter.

The present invention makes it possible to provide a stent that has high reliability to prevent an opaque member from coming off in a luminal structure and includes a strut and an opaque member attached to the strut with a high level of ease of attachment.

DETAILED DESCRIPTION OF THE INVENTION

[Basic Form]

Hereinafter, stents according to embodiments of the present invention will be described with reference to the drawings. Prior to the description of embodiments, the overall structure of a stent in a first basic form without inventive features will be described with reference to FIGS. 1 to 9. According to embodiments of the present invention, for example, an inventive feature or features are added to the basic form. Such inventive features will be described with reference to, for example, FIGS. 10 to 18.

Figure 1:
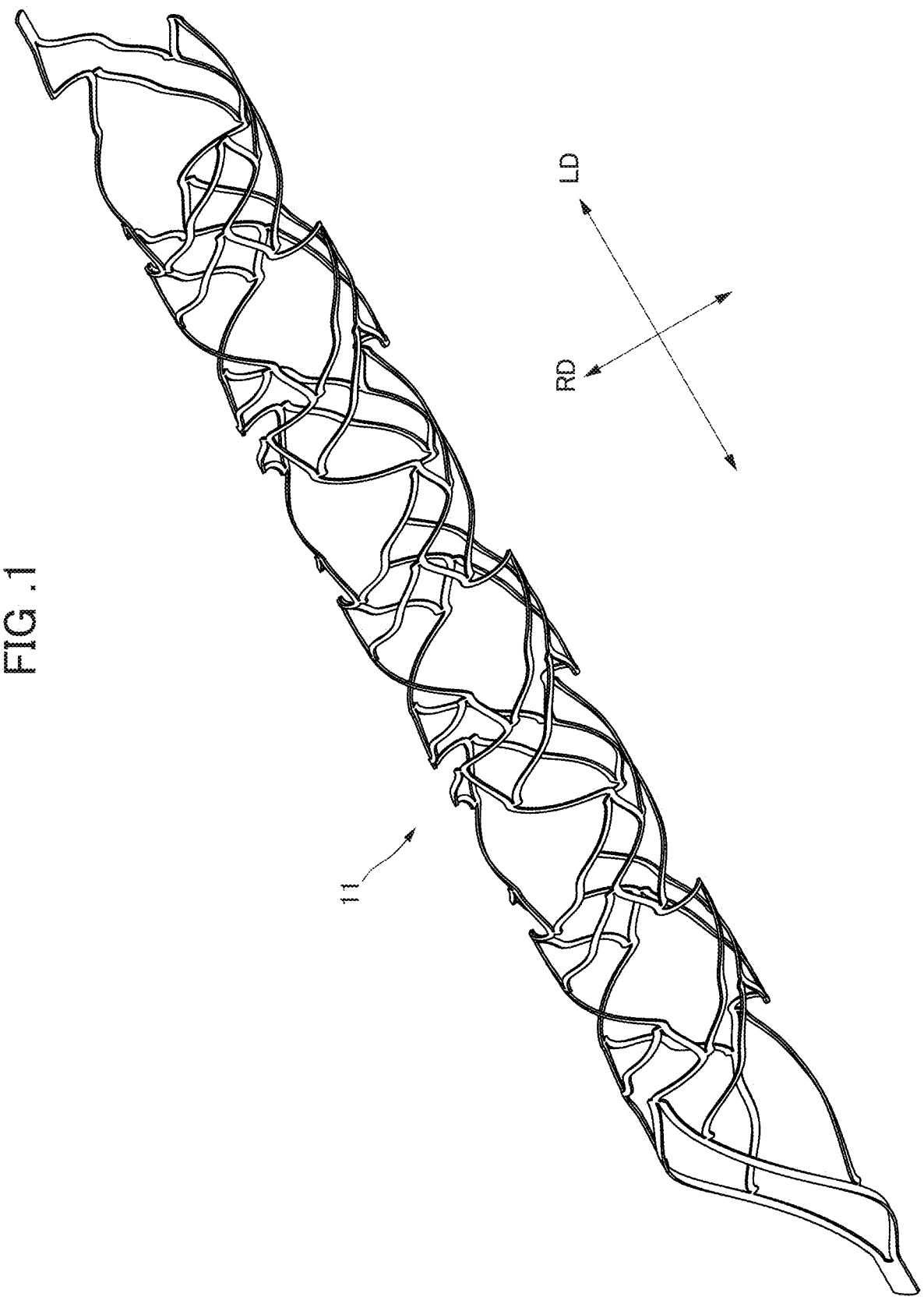
FIG. 1 is a perspective view of a stent in a basic form under unloaded conditions.
Figure 2:
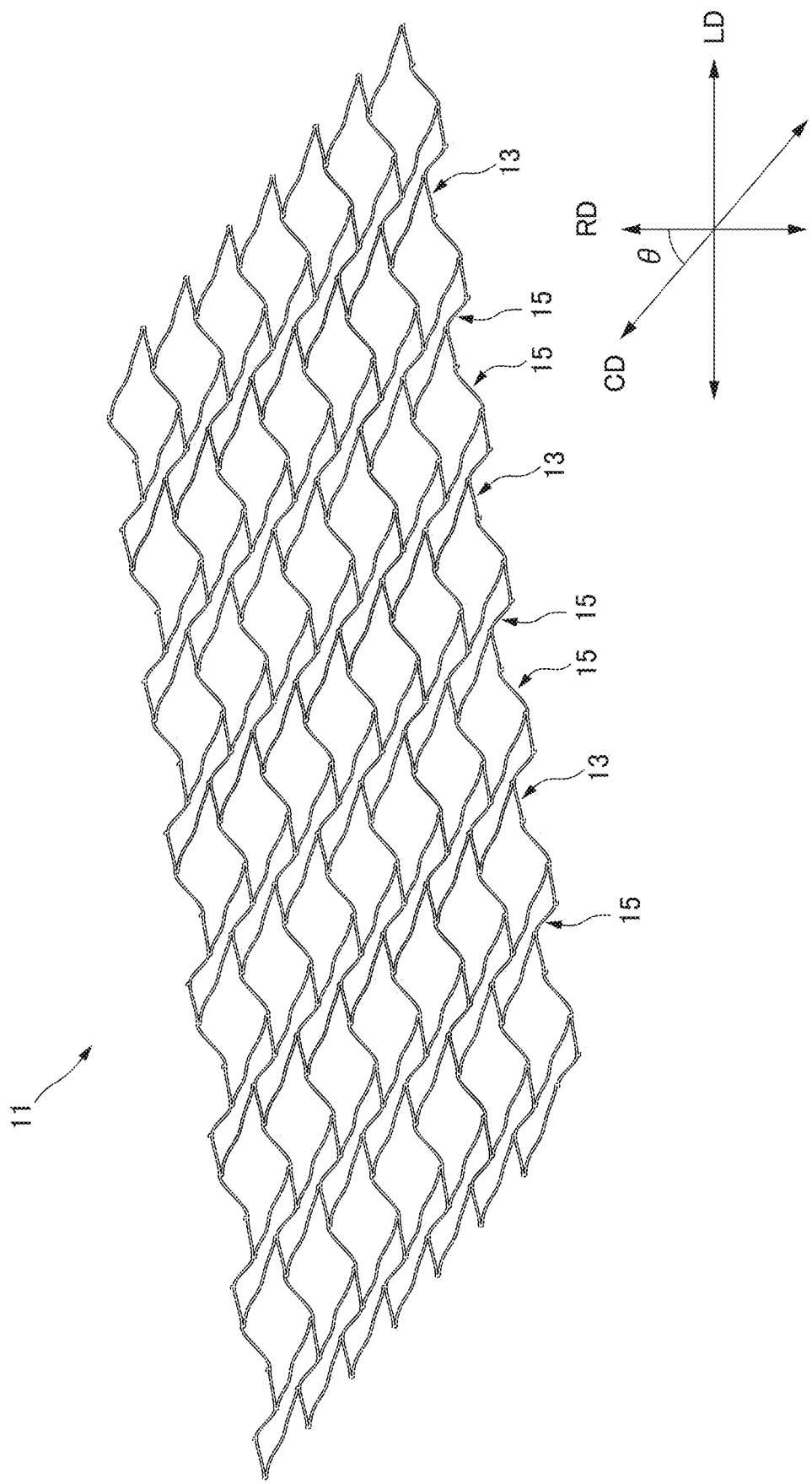
FIG. 2 is a developed view showing repeated patterns of the stent in a basic form under unloaded conditions, in which the stent is virtually developed in a plane.
Figure 3:
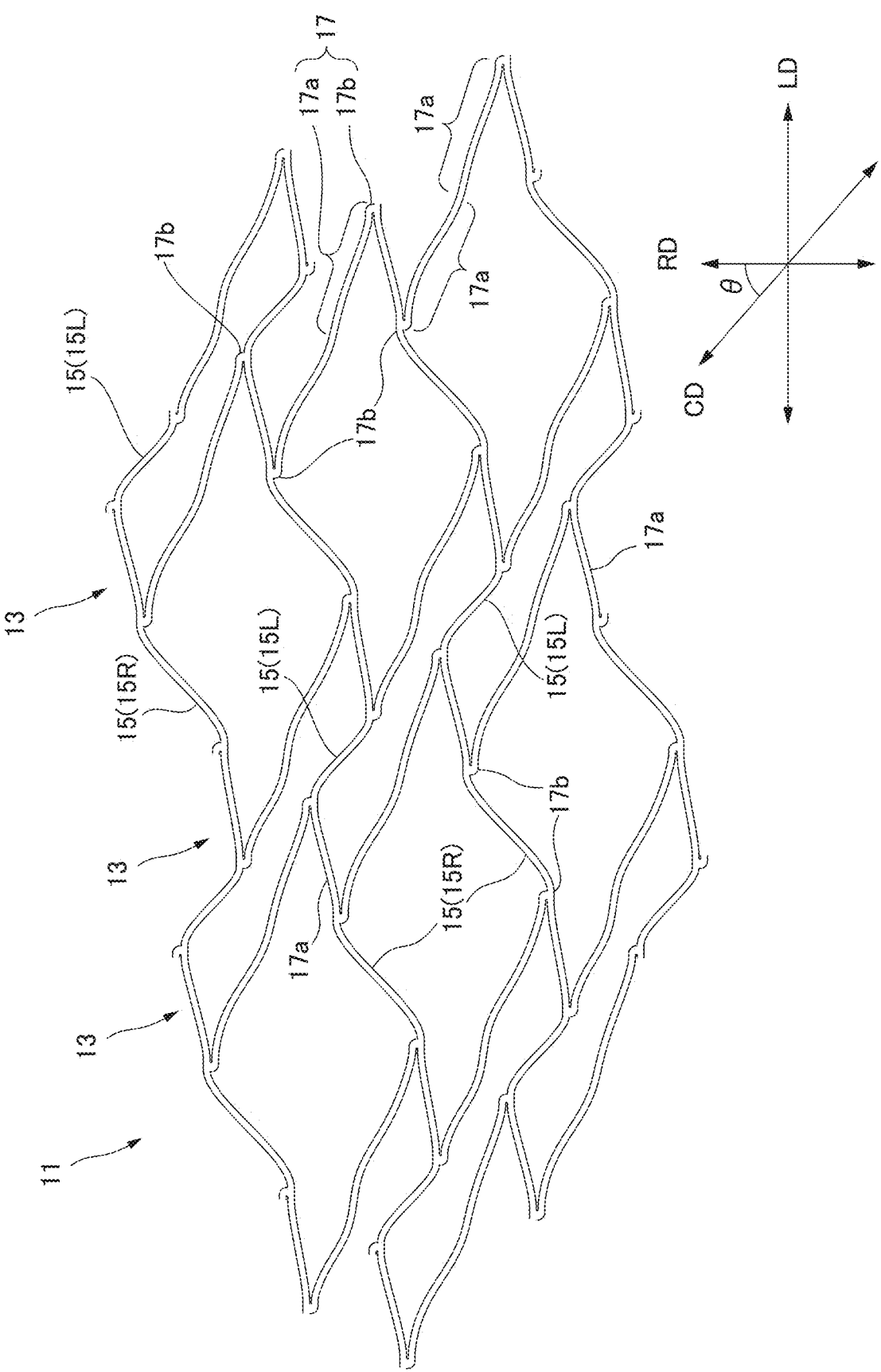
FIG. 3 is a partially enlarged view of the stent shown in FIG. 2.
Figure 4:
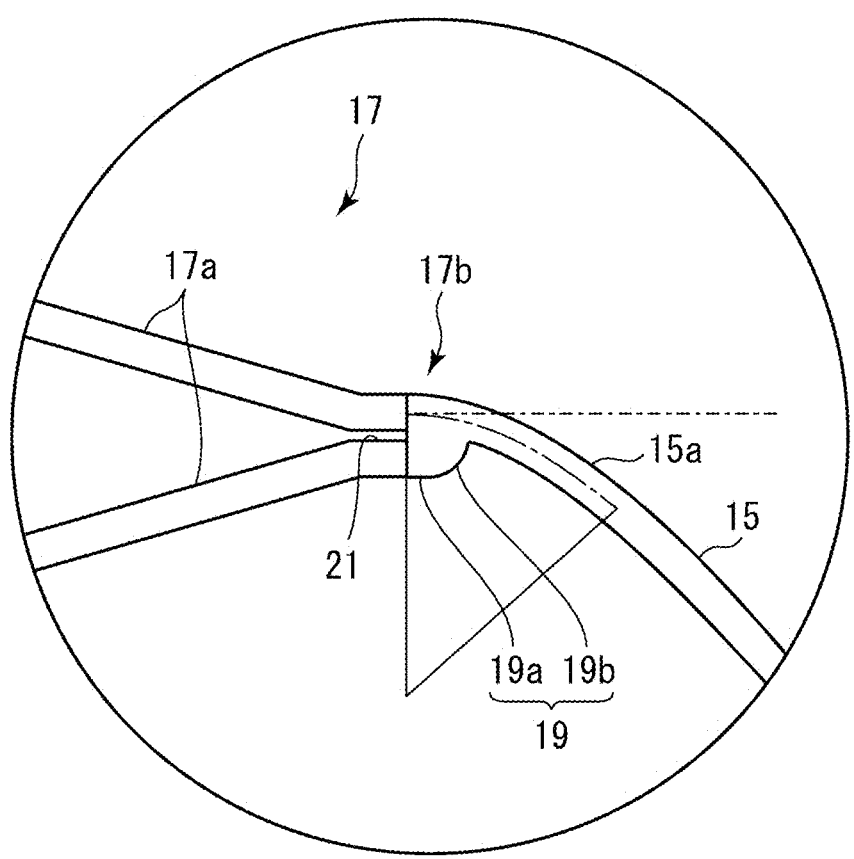
FIG. 4 is a partially enlarged view of the stent shown in FIG. 3.
Figure 5:
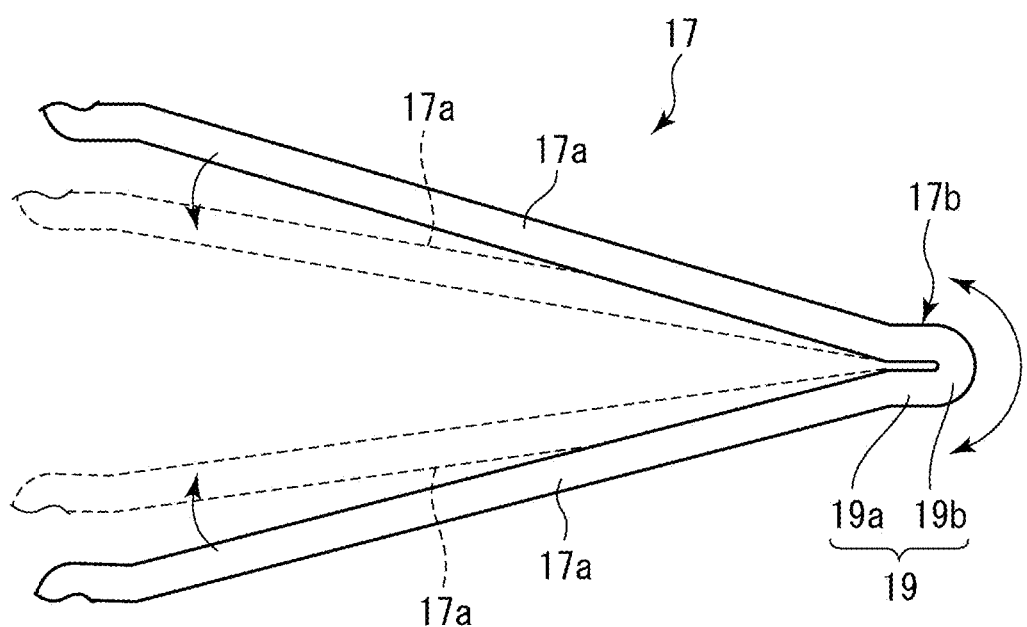
FIG. 5 is an illustrative view showing that a top portion of a crimp element of a ring in a stent can deform when the stent is radially compressed.
Figure 6A:
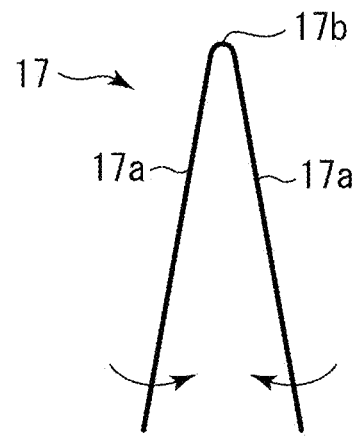
FIG. 6A is a schematic diagram showing how a crimp element of a ring in a stent can deform when the stent is radially compressed in a case where a top portion of the crimp element has no slit.
Figure 6B:
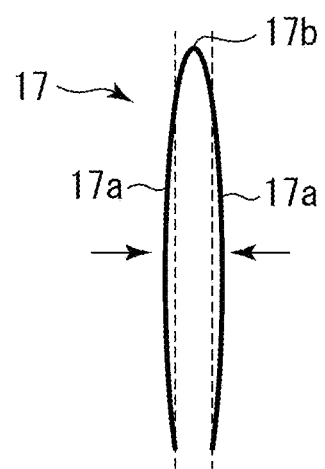
FIG. 6B is a schematic diagram showing how a crimp element of a ring in a stent can deform when the stent is radially compressed in a case where a top portion of the crimp element has no slit.
Figure 7A:
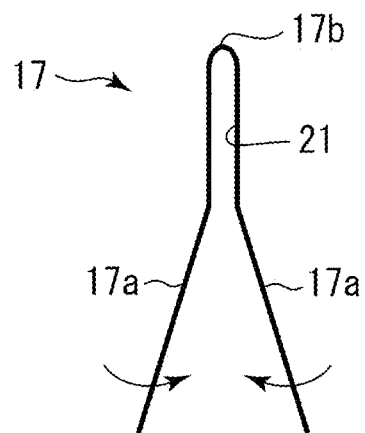
FIG. 7A is a schematic diagram showing how a crimp element of a ring in a stent can deform when the stent is radially compressed in a case where a top portion of the crimp element has a slit.
Figure 7B:
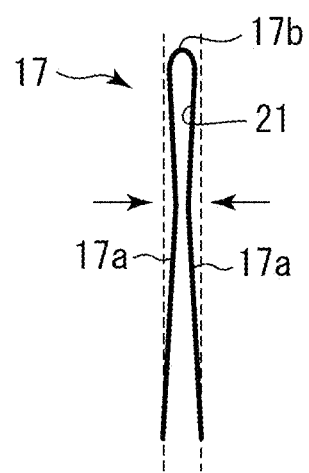
FIG. 7B is a schematic diagram showing how a crimp element of a ring in a stent can deform when the stent is radially compressed in a case where a top portion of the crimp element has a slit.
Figure 8:
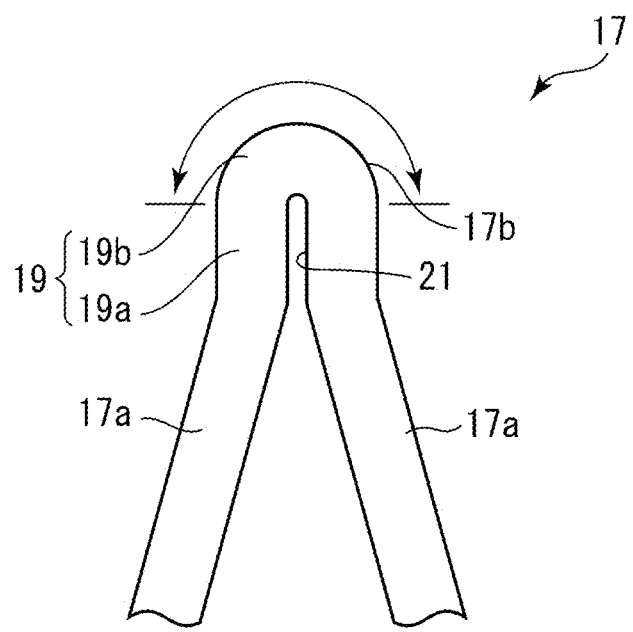
FIG. 8 is a partially enlarged view showing a first form of a top portion of a crimp element of a ring in a stent.
Figure 9:
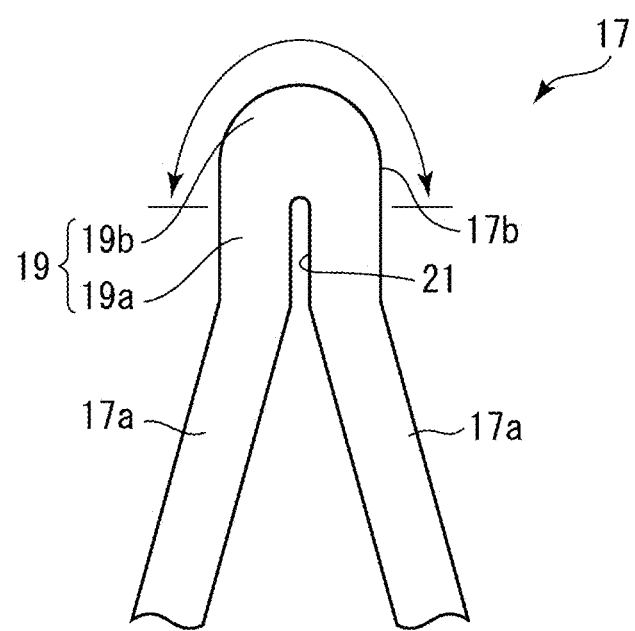
FIG. 9 is a partially enlarged view showing a second form of a top portion of a crimp element of a ring in a stent.

FIG. 1 is a perspective view of a stent in a basic form under unloaded conditions. FIG. 2 is a developed view showing repeated patterns of the stent in a basic form under unloaded conditions, in which the stent is virtually developed in a plane. FIG. 3 is a partially enlarged view of the stent shown in FIG. 2. FIG. 4 is a partially enlarged view of the stent shown in FIG. 3. FIG. 5 is an illustrative view showing that a top portion of a crimp element of a ring in a stent can deform when the stent is radially compressed. FIGS. 6A and 6B are schematic diagrams showing how a crimp element of a ring in a stent can deform when the stent is radially compressed in a case where a top portion of the crimp element has no slit. FIGS. 7A and 7B are schematic diagrams showing how a crimp element of a ring in a stent can deform when the stent is radially compressed in a case where a top portion of the crimp element has a slit. FIG. 8 is a partially enlarged view showing a first form of a top portion of a crimp element of a ring in a stent. FIG. 9 is a partially enlarged view showing a second form of a top portion of a crimp element of a ring in a stent.

As shown in FIG. 1, a stent 11 is substantially cylindrical. The circumferential wall of the stent 11 has a mesh-pattern structure in which plural closed cells being congruent in shape and each made of a wire-shaped material surrounding the cell are closely arranged in the circumferential direction. FIG. 2 is to facilitate the comprehension of the structure of the stent 11, in which the stent 11 is shown in a form developed in a plane. To show the periodicity of the mesh patterns, FIG. 2 virtually illustrates more repeated mesh patterns than those in the actual developed state. As used herein, the term "the circumferential wall of the stent 11" means a portion that separates the inside of the substantially cylindrical structure of the stent 11 from the outside. As used herein, the term "cell" refers to a portion surrounded by a wire-shaped material, which forms the mesh patterns of the stent 11 and is also called an opening or a compartment.

The stent 11 is made of stainless steel or a biocompatible material such as tantalum, platinum, gold, cobalt, titanium, or any alloy thereof. In particular, the stent 11 is preferably made of a superelastic material such as a nickel-titanium alloy.

The stent 11 includes rings 13 that are arranged side by side in the longitudinal axis direction LD (namely, the central axis direction) to form plural crimp patterns; and plural coiled elements 15 each disposed as a connecting element between the rings 13 adjacent to each other in the longitudinal axis direction LD. As shown in FIG. 3, each ring 13 includes plural substantially V-shaped crimp elements 17 each including two leg portions 17a and a top portion 17b through which the two leg portions 17a are connected, in which the plural crimp elements 17 are connected in the circumferential direction to form a crimp pattern. Specifically, the substantially V-shaped crimp elements 17 are connected with the top portions 17b disposed on sides opposite to each other.

When viewed in the radial direction RD perpendicular to the axial direction LD, the cyclic direction CD of the rings 13 is inclined with respect to the radial direction RD. The cyclic direction CD of the rings 13 is inclined at angle θ of, for example, 30 to 60 degrees with respect to the radial direction RD.

Both ends of each coiled element 15 are connected to the opposing top portions 17b of two adjacent rings 13. In this regard, each pair of the opposing top portions 17b of the adjacent rings 13 are connected to each another through each coiled element 15. The stent 11 has what is called a closed cell structure. Specifically, two top portions 17b adjacent to each other along the crimp pattern among three top portions 17b connected through leg portions 17a along the crimp pattern in one of adjacent rings 13 are connected through coiled elements 15 to two top portions 17b adjacent to each other along the crimp pattern among three top portions 17b connected through leg portions 17a along the crimp pattern in the other of the adjacent rings 13 to form a cell. Each top portion 17b of each ring 13 in the crimp pattern is shared by three cells.

The plural coiled elements 15 are arranged at equal intervals along the axis direction LD. Each coiled element 15 extends spirally around the central axis. As shown in FIG. 3, the winding direction (right-handed) of one (15R) of the coiled elements 15 located on one side with respect to the ring 13 in the axis direction LD is reverse to the winding direction (left-handed) of the other (15L) of the coiled elements 15 located on the other side in the axis direction LD. The length of one coiled element 15R is larger than that of the leg portion 17a but not larger than 1.5 times that of the leg portion 17a. The length of the other coiled element 15L is smaller than that of the leg portion 17a.

In the present invention, the cyclic direction CD of the rings 13 may not be inclined with respect to the radial direction RD (the cyclic direction CD may be parallel to the radial direction RD). Some of the top portions 17b may not be connected through the coiled elements 15 (connecting elements). The connecting element may not extend spirally around the axis LD or may be linear or substantially linear.

Each end portion of each coiled element 15 has a curved portion 15a. Each end portion of each coiled element 15 is connected through the curved portion 15a to each of the opposing top portions 17b (specifically bulges 19 of them)

of two adjacent rings 13. As shown in FIG. 4, the curved portion 15a of each end portion of the coiled element 15 has an arc shape. The coiled element 15 has a tangential direction at the connection end between the coiled element 15 and the top portion 17b of the ring 13 in the crimp pattern, and the tangential direction is coincident with the longitudinal axis direction LD.

The transverse center of the end portion of the coiled element is offset from (not coincident with) the peak (transverse center) of the top portion 17b of the ring 13. One transverse edge of the end portion of the coiled element 15 is coincident with a transverse edge of the top portion 17b of the ring 13.

The stent 11 with the structure described above not only has a high ability to conform to shape and to be radially compressed but also resists metal fatigue-induced breakage. In the stent 11, the bulge 19 provided in the top portion 17b of the crimp element 17 of the ring 13 is effective in reducing metal fatigue. In the stent 11, a slit 21 extends from an inner peripheral edge of the top portion 17b of the crimp element 17 of the ring 13. The slit 21 is effective in increasing the ability of the stent 11 to be radially compressed.

The conventional stent with a closed-cell structure is structurally less flexible and thus may buckle in a bent blood vessel to hinder blood flow. Moreover, if such a stent is locally deformed, the influence of its deformation will propagate not only in the radial direction RD of the stent but also in the longitudinal axis direction LD of the stent, which makes it impossible for the stent to undergo local deformation independently. Due to this, such a stent may fail to conform to a complex vascular structure such as an aneurysm, so that a gap may occur between the circumferential wall of the stent and the vascular wall and that the stent may be more slidable in the vascular lumen as the blood vessel deforms in association with the pulsation, which may cause migration of the stent after placement.

In contrast, when the stent 11 in the basic form is deformed from an expanded state to a radially compressed state (crimped state), the crimp pattern of the ring 13 is compressed so as to be folded and the coiled element 15 is tilted to the longitudinal axis direction LD so as to be pulled in the longitudinal axis direction LD like a coil spring. Considering one of the crimp elements 17 of the ring 13 in the crimp pattern in the stent 11, the crimp element 17 deforms as shown in FIG. 5, like opening and closing tweezers, when the stent 11 is radially compressed and expanded.

In a case as shown in FIG. 6A where no slit 21 is provided at a V-shaped base portion of the crimp element 17 (at an inner peripheral edge of the top portion 17b), the central portions of the leg portions 17a tend to deform to bulge outward like a barrel shape as shown in FIG. 6B when the stent 11 is radially compressed so that the crimp element 17 is deformed to be closed. If the crimp element 17 deforms to bulge in a barrel shape, the barrel-like bulging leg portions 17a of the crimp elements 17 circumferentially adjacent to each other in the rings 13 will come into contact with each other in the stent 11 being compressed radially.

This contact will hinder the radial compression of the stent 11 (in particular, the rings 13), which will lead to a lower radial compression rate. On the other hand, in the stent 11 in the basic form, a slit 21 is provided as shown in FIG. 7A at a base portion of the crimp element 17 of the ring 13. Therefore, as shown in FIG. 7B, the stent 11 can deform so that the leg portions 17a of the crimp elements 17 circumferentially adjacent to each other in the rings 13 are less likely to come into contact with each other when the stent 11 is radially compressed, which will lead to a higher radial compression rate.

As described above, the crimp element 17 deforms like opening and closing tweezers as shown in FIG. 5 when the stent 11 is radially compressed and expanded. Therefore, when the stent 11 is crimped or expanded, the deformation is concentrated on the top portions to cause strain intensively in these portions due to material deformation. Therefore, excessive metal fatigue is likely to occur in the top portion 17b of the crimp element 17 when the stent 11 is repeatedly compressed radially and repeatedly expanded or when the stent 11 is subjected to repeated loading as it is deformed due to the blood flow in the vessel or the pulsation of the vascular wall. In the stent 11, therefore, the top portion 17b has an improved shape to reduce the risk of causing metal fatigue and to reduce strain in the top portion 17b.

When the stent 11 is radially compressed and expanded, the crimp element 17 closes and opens around the V-shaped base portion (at the inner peripheral edge). In the top portion 17b of the crimp element 17, therefore, strain often occurs particularly at the outer peripheral edge (an outer portion of the top portion 17b indicated by the curve with arrows at both ends in FIG. 5). In this case, the strain may be expressed by the formula below, in which e is the strain, l0 (el zero) is the undeformed length, and u is the amount of deformation.

$$e = u/l0$$

Therefore, in order to reduce the risk of occurrence of metal fatigue in the top portion 17b of the stent 11, the strain should be reduced in the top portion 17b when the stent 11 is radially compressed and expanded.

If the amount u of deformation is given at the same level during the radial compression, the length corresponding to l0 may be increased so that the strain can be reduced in the top portion 17b. Moreover, the crimp element 17 deforms mainly at its V-shaped base portion (inner peripheral edge), and the portion that substantially contributes to the deformation is the protruding side of the top portion 17b of the crimp element 17 (in the range indicated by the two-way arrow on the top side in FIGS. 8 and 9), particularly its outer peripheral edge. As shown in FIGS. 8 and 9, therefore, in the stent 11, the bulge 19 is formed in the top portion 17b to extend the top portion 17b in the longitudinal axis direction LD. The bulge 19 includes an extension portion 19a and a substantially semicircular portion 19b and has a width larger than that of the coiled element 15.

Specifically, in the crimp element 17, the extension portion 19a extending in the longitudinal axis direction LD is provided between the leg portion 17a and the substantially semicircular portion 19b in the top portion 17b to offset the top portion 17b toward the outside from the V-shaped base portion (inner peripheral edge) of the crimp element 17, which provides a deformation base point. This lengthens the outer peripheral edge of the top portion 17b. As shown in FIGS. 8 and 9, the extension portion 19a preferably includes a linear portion extending in the longitudinal axis direction LD so that, during the radial compression, the bulges 19 circumferentially adjacent to each other can be prevented from contacting with each other, which would otherwise hinder the radial compression.

Incidentally, when the top portion 17b of the crimp element 17 has the slit 21 extending from the inner peripheral edge of the top portion 17b, the crimp element 17 can deform around the front end of the slit 21 (the top end of the slit 21 in FIGS. 8 and 9) as shown in FIGS. 7A and 7B. The portion mainly involved in the deformation associated with crimping and expansion is located outside the top end of the slit 21 in the crimp element 17. Therefore, the mode shown in FIG. 9 in which the extension portion 19*a* is longer than the slit 21 and extends beyond the top end of the slit 21 is better than the mode shown in FIG. 8 in which the length of the extension portion 19*a* is equal to or smaller than that of the slit 21.

As shown in FIGS. 8 and 9, the slit 21 has opposing side edges that linearly extend substantially in parallel to each other. Alternatively, the slit 21 may have opposing side edges extending not substantially in parallel to each other (e.g., slightly expanding toward the leg portion 17*a* (not shown)). Alternatively, the slit 21 may have non-linear opposing side edges (not shown).

Furthermore, when the stent 11 is made of a superelastic alloy such as a nickel-titanium alloy, the stent 11 may be configured such that, as shown in FIG. 9, the bulge 19 is provided in the top portion 17*b* of the crimp element 17 of the ring 13 and the extension portion 19*a* of the bulge 19 has a length larger than that of the slit 21. This allows the superelastic alloy to exhibit the superelastic properties to the full and reduces variations in expansion force with different outer diameters of the stent 11.

When the stent 11 is configured such that the slit 21 is provided in the top portion 17*b* of the crimp element 17 of the ring 13 and the extension portion 19*a* of the bulge 19 in the top portion 17*b* has a length larger than that of the slit 21, the portion around the slit 21 can have a higher volume ratio of the material capable of undergoing martensitic phase transformation during loading. Therefore, the stent 11 configured to include the crimp element 17 having the top portion 17*b* as shown in FIG. 9 can be such that the expansion force gradually changes as the diameter of the stent 11 changes so that changes in expansion force with different vascular diameters are small.

In the stent 11, the curved portions 15*a* provided at both ends of the coiled element 15 are effective in allowing the coiled element 15 to deform more smoothly at the connection with the ring 13 and effective in increasing the ability of the stent 11 to be radially compressed.

When the stent 11 is radially compressed, the coiled element deforms to extend in the longitudinal axis direction LD. Therefore, to increase the flexibility of the stent 11, it is necessary to design a flexible connection between the top portion 17*b* of the ring 13 and the coiled element 15. In the stent 11, the coiled element 15 has the curved portions 15*a* in an arc shape at both ends, and the top portion 17*b* of the ring 13 is connected to the coiled element 15 through the curved portion 15*a*. When the stent 11 is radially compressed, the curved portions 15*a* deform due to bending to allow the coiled element 15 to deform flexibly, which enhances the ability to be radially compressed.

Furthermore, the curved portion 15*a* has a tangential direction coincident with the longitudinal axis direction LD at the connection end between the coiled element 15 and the top portion 17*b* of the ring 13. This configuration is effective in facilitating the deformation associated with the radial compression and expansion of the stent 11 and effective in slowing the change in expansion force with different diameters of the stent 11.

The coiled element 15 deforms like a coil spring to extend in the longitudinal axis LD, which allows deformation in the radial direction RD in association with the radial compression of the stent 11. Accordingly, the deformation characteristics of the coiled element 15 in the longitudinal axis direction LD can be effectively exhibited when the curved portion 15*a* has a tangential direction coincident with the longitudinal axis direction LD at the connection end between the ring 13 and the coiled element 15. The coiled element 15 is allowed to deform smoothly in the longitudinal axis LD, so that the stent 11 can be easily radially compressed and expanded. Natural deformation of the coiled element 15 is also facilitated in the longitudinal axis direction LD, which is effective in preventing unexpected deformation resistance and effective in slowing the response of expansion force to the change in the diameter of the stent 11.

The stent 11 in a radially compressed state is inserted into a catheter, pushed by a pushing machine such as a pusher to move through the catheter, and deployed at a lesion site. In this process, the force applied in the longitudinal axis direction LD by the pushing machine is transmitted throughout the stent 11 while providing interaction between the ring 13 and the coiled element 15 in the stent 11.

Next, a method for using the stent 11 will be described. A catheter is inserted into a blood vessel in the patient and allowed to reach a lesion site. The stent 11 is then radially compressed (crimped) and placed in the catheter. The stent 11 has an increased ability to be radially compressed, which is due to the combined or synergetic effect of the crimp pattern of the ring 13, the slit 21 formed in the top portion 17*b* of the ring 13, the curved portion 15*a* of the coiled element 15, and the tangential direction of the curved portion 15*a* coincident with the longitudinal axis direction LD at the connection end. This makes it easy to insert the stent 11 into a thinner catheter as compared to the conventional stent and makes it possible to use the stent 11 in thinner blood vessels.

The stent 11 in a radially compressed state is then pushed along the lumen of the catheter using a pushing machine such as a pusher. At a lesion site, the stent 11 is pushed out of the distal end of the catheter and expanded (deployed). The stent 11 has increased flexibility during delivery, which is due to the combined or synergetic effect of the connection of plural rings 13 by the coiled elements 15, the curved portion 15*a* of the coiled element 15, and the tangential direction of the curved portion 15*a* coincident with the longitudinal axis direction LD at the connection end. Therefore, even when the catheter is inserted in a tortuous blood vessel, the stent 11 can flexibly deform along the catheter and can be easily delivered to the lesion site.

Furthermore, in the stent 11, the top portion 17*b* of the ring 13 has the bulge 19, which can prevent metal fatigue and breakage of the stent 11 caused by repetition of radial compression and expansion of the stent 11 due to placement mistake or caused by repetition of deformation of the stent 11 due to the blood flow or the pulsation of the vascular wall.

Moreover, the stent 11 has increased flexibility and allows the expansion force to gently change in response to the change in the diameter of the stent 11 during the unloading process, which is due to the combined or synergetic effect of: the slit 21 provided in the top portion 17*b* of the ring 13 to increase the region capable of undergoing martensitic phase transformation in the portion deformed during crimping; the curved portion 15*a* of the coiled element 15; and the tangential direction of the curved portion 15*a* coincident with the longitudinal axis direction LD at the connection end. This results in an increase in the shape conformity of the stent 11 and makes it possible to place the stent 11 with no excessive load on the blood vessel even at a site where the vascular diameter locally changes, such as a tapered blood vessel.

It should be noted that the features described above are non-limiting features of the stent 11 in the basic form. For example, the length of one coiled element 15R may be the same as the length of the other coiled element 15L. Both the length of one coiled element 15R and the length of the other coiled element 15L may be larger or smaller than the length of the leg portion 17a. The spiral direction of the coiled element 15 may be left-handed or right-handed.

In the basic form, the crimp pattern unit 13 forms a ring. Alternatively, in the present invention, non-ring-forming crimp pattern units 13 may be used, which are circumferentially discontinuous. The non-ring-forming crimp pattern unit 13 lacks one or more struts (leg portions 17a) for forming the crimp pattern as compared to the ring-forming crimp pattern unit. Any appropriate number of struts may be removed as long as the shape of the stent 11 can be established.

[Pattern of Arrangement of Opaque Members]

Figure 10:
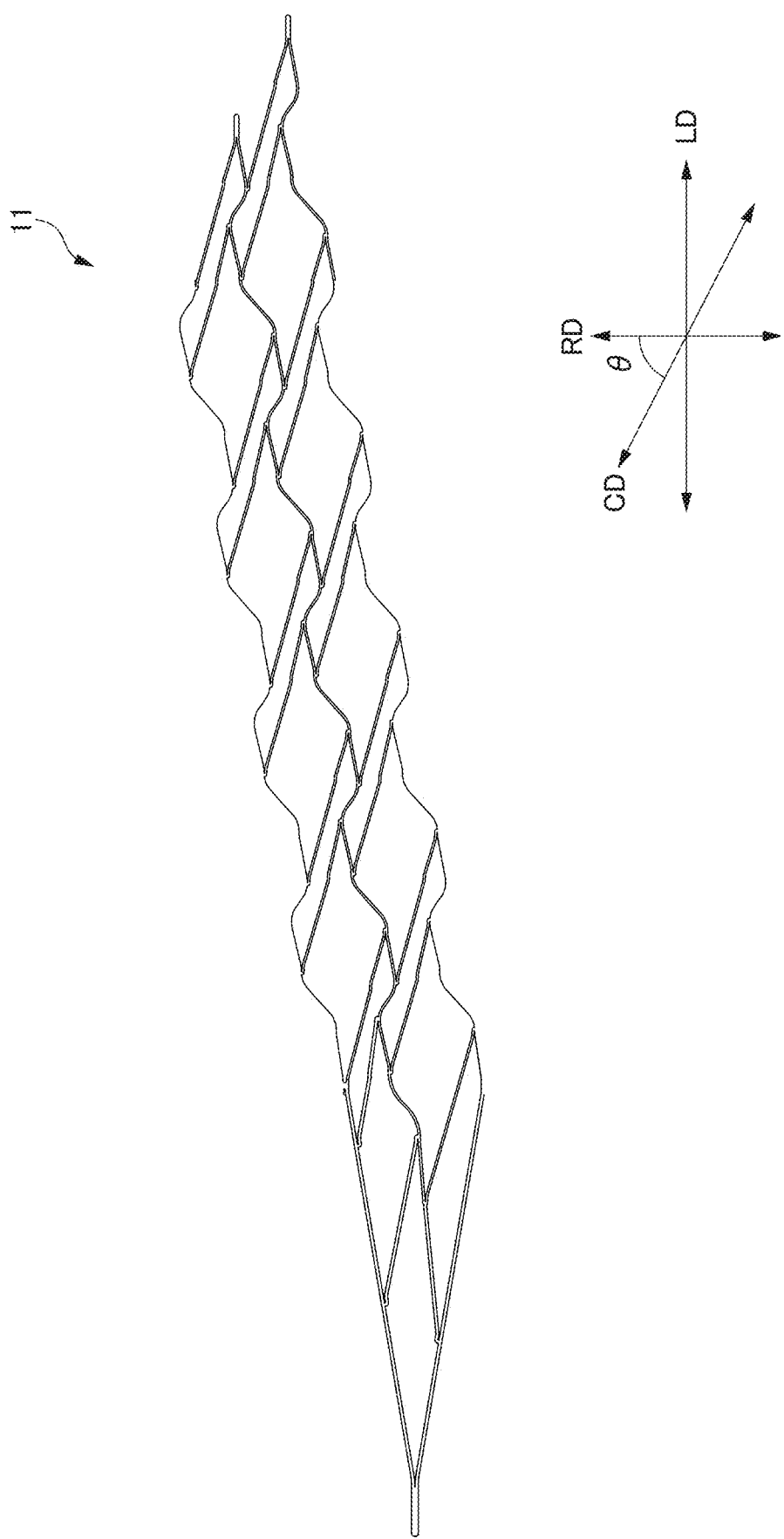
FIG. 10 is an actual developed view of the stent in the basic form shown in FIG. 1.
Figure 11:
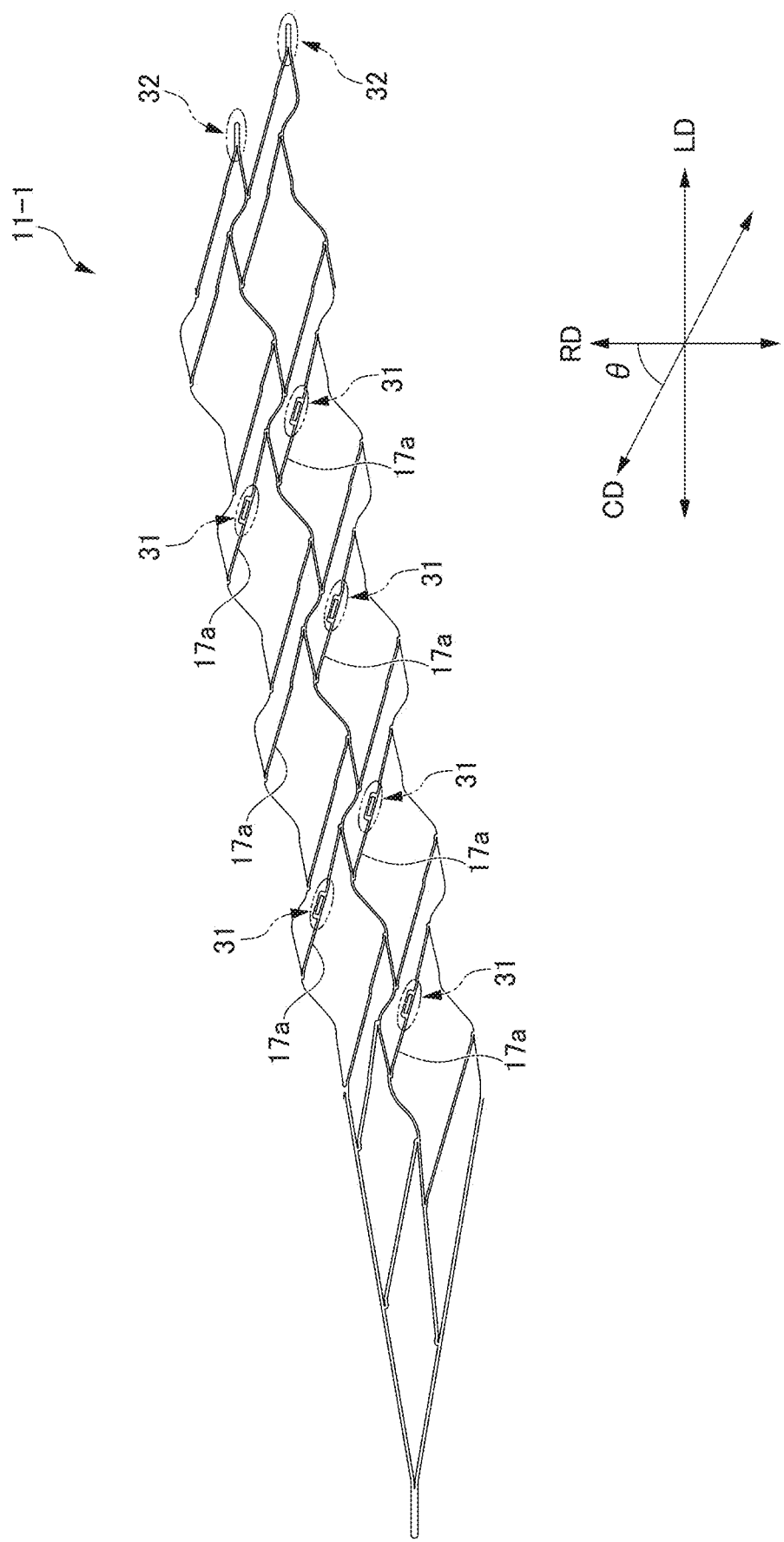
FIG. 11 is a view showing a first pattern in which opaque members are arranged.
Figure 12:
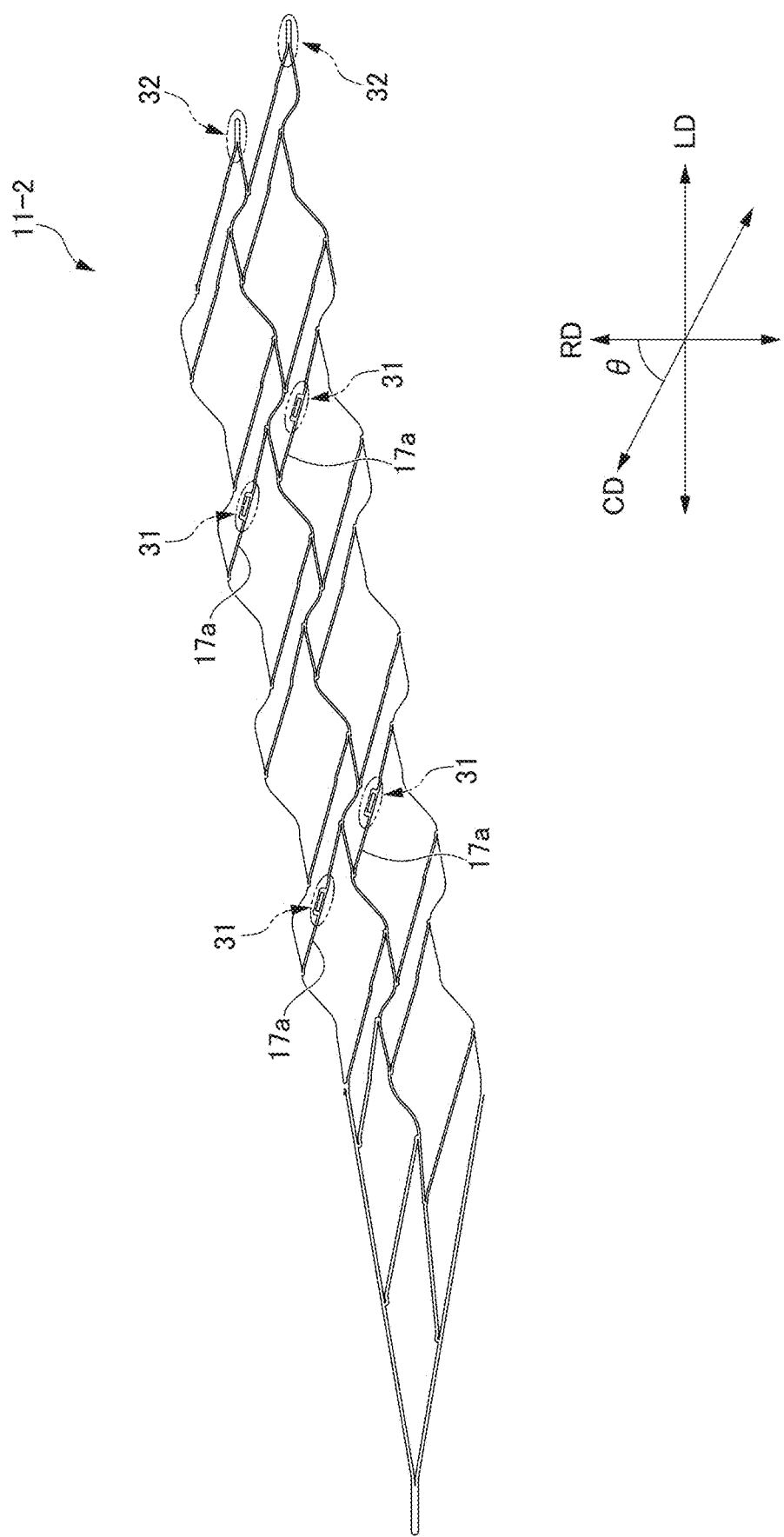
FIG. 12 is a view showing a second pattern in which opaque members are arranged.
Figure 13:
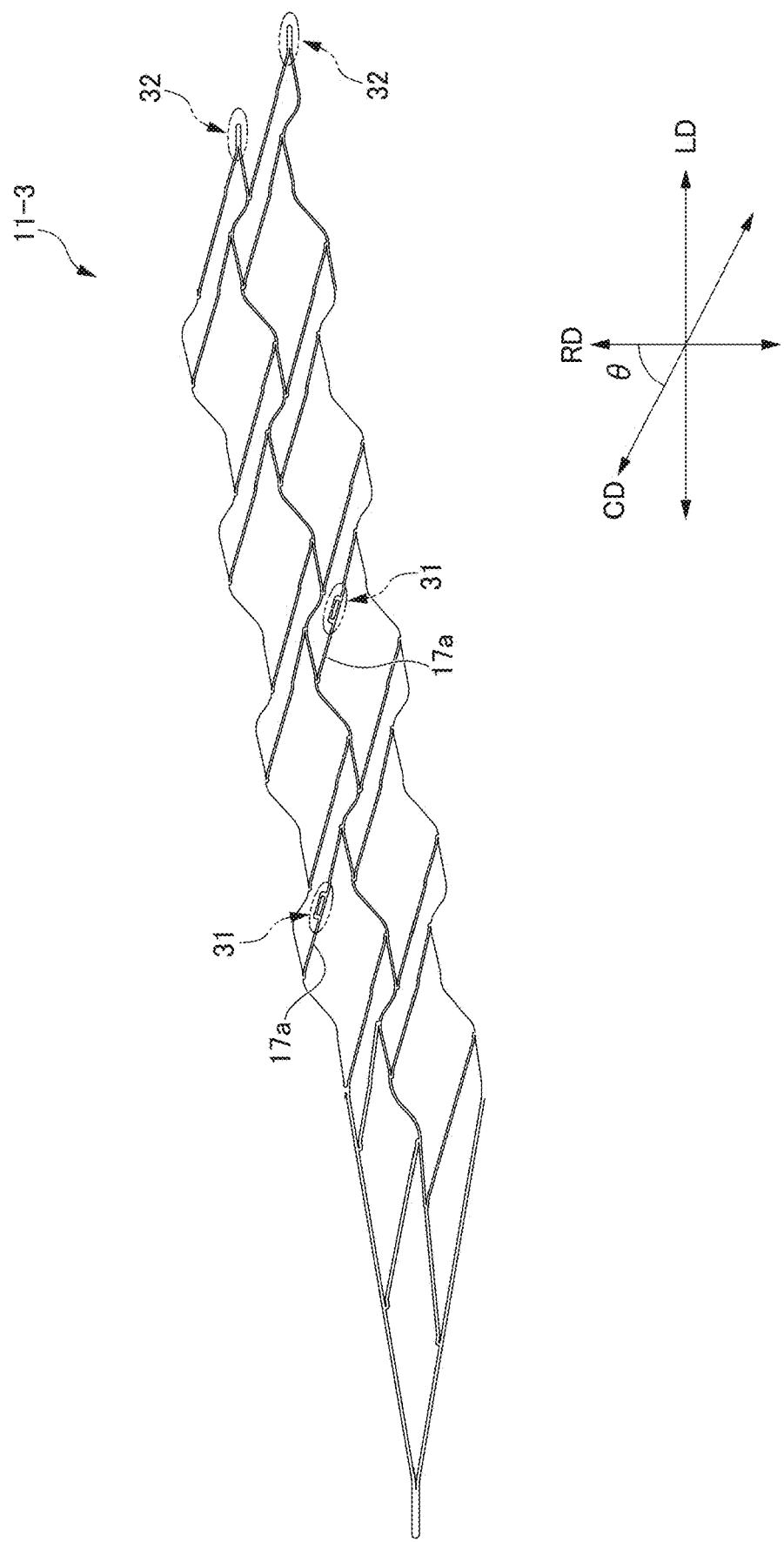
FIG. 13 is a view showing a third pattern in which opaque members are arranged.
Figure 14:
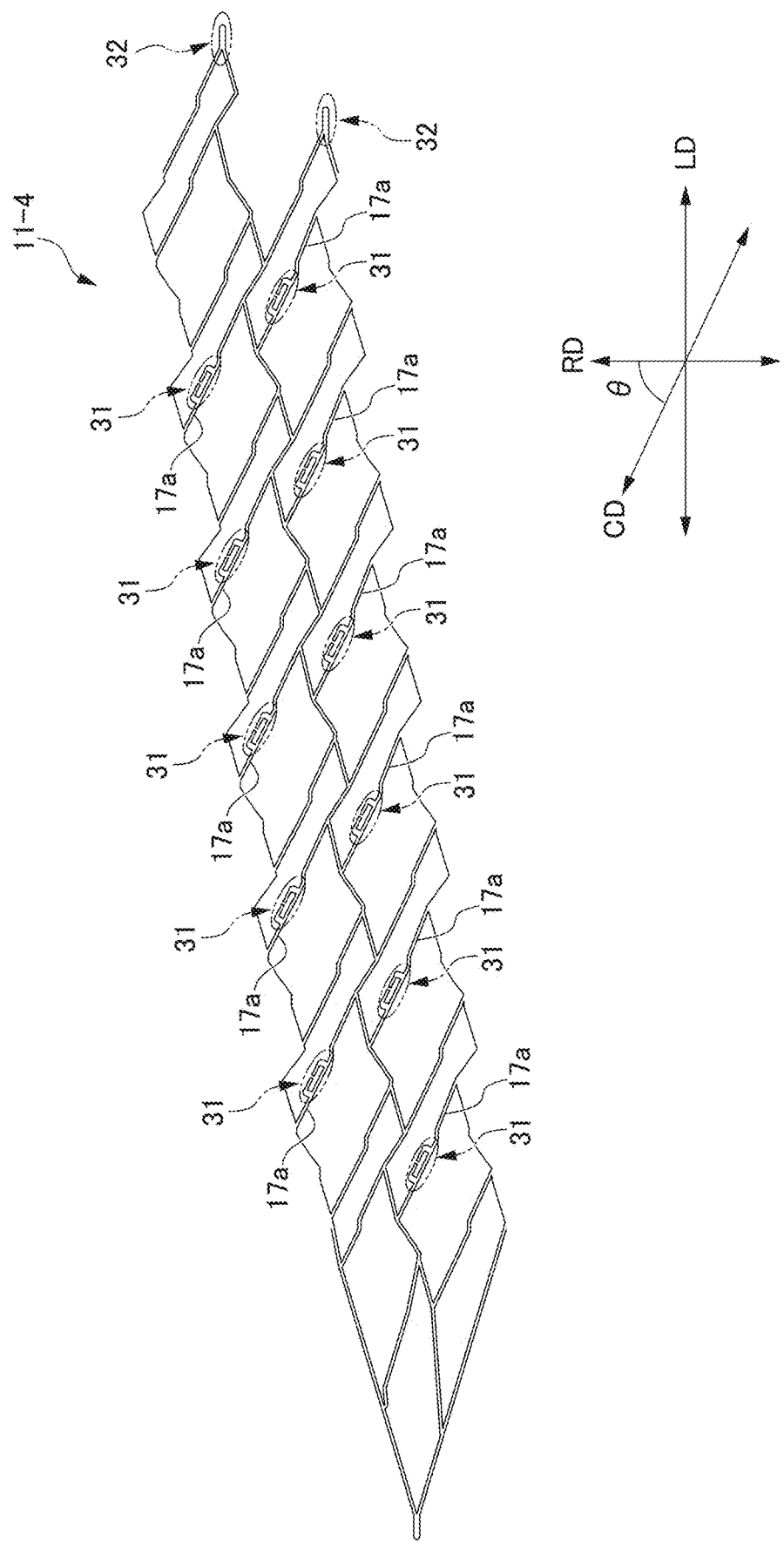
FIG. 14 is a view showing a fourth pattern in which opaque members are arranged.
Figure 15:
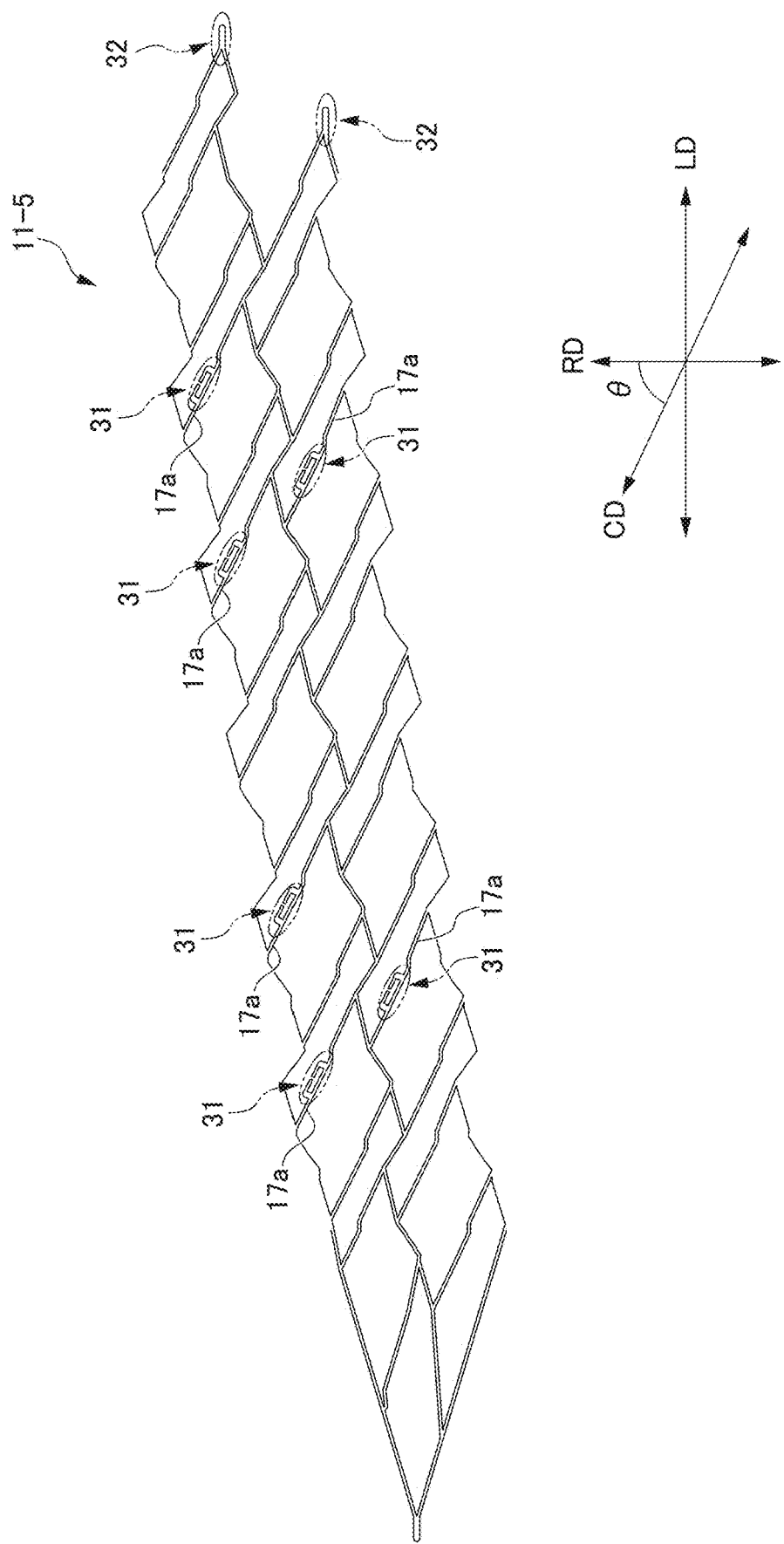
FIG. 15 is a view showing a fifth pattern in which opaque members are arranged.
Figure 16:
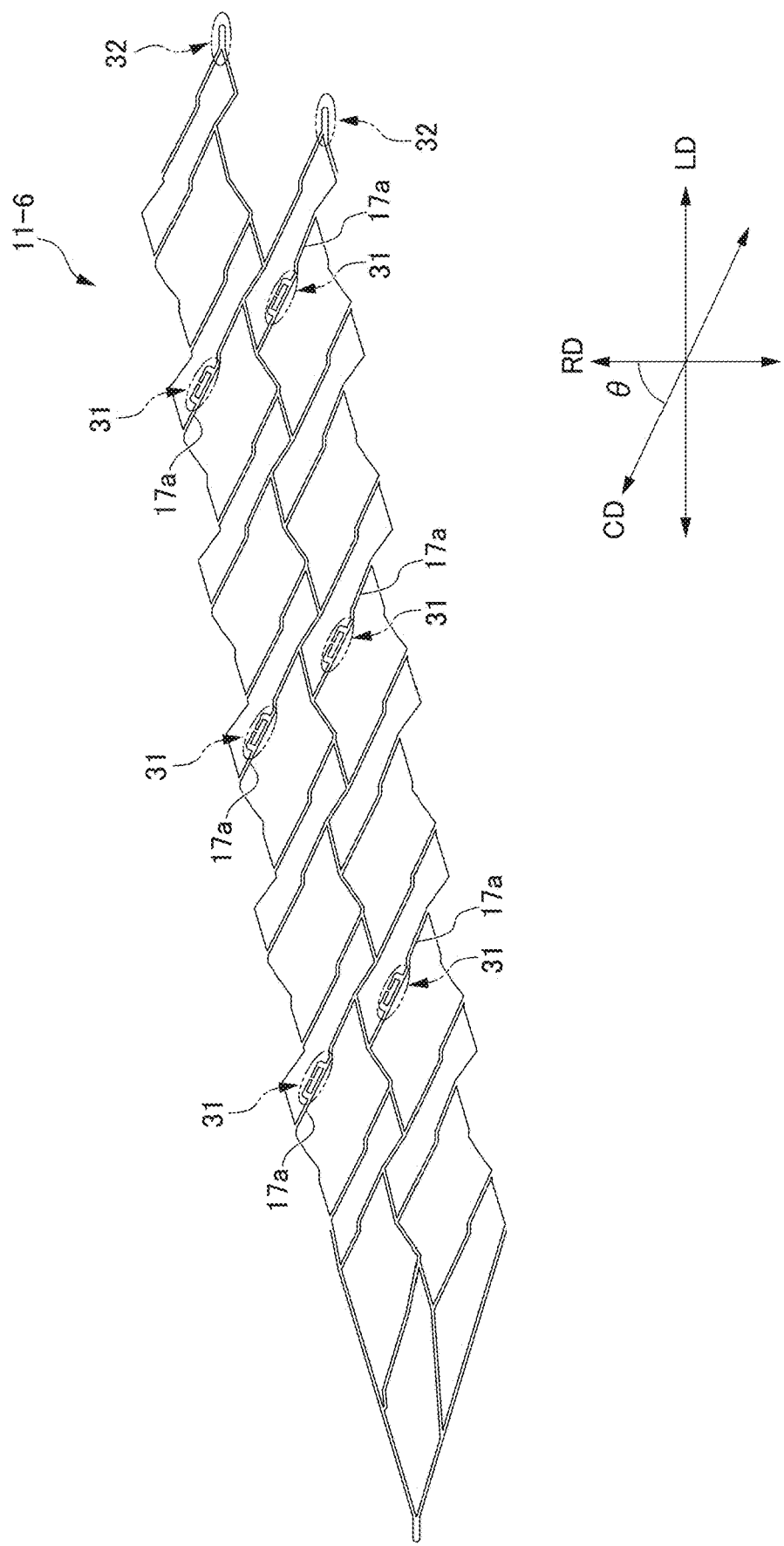
FIG. 16 is a view showing a sixth pattern in which opaque members are arranged.

Next, variations in the pattern of arrangement of opaque members will be described with reference to FIGS. 10 to 16. FIG. 10 is an actual developed view of the stent in the basic form shown in FIG. 1. FIG. 11 is a view showing a first pattern in which opaque members are arranged. FIG. 12 is a view showing a second pattern in which opaque members are arranged. FIG. 13 is a view showing a third pattern in which opaque members are arranged. FIG. 14 is a view showing a fourth pattern in which opaque members are arranged. FIG. 15 is a view showing a fifth pattern in which opaque members are arranged. FIG. 16 is a view showing a sixth pattern in which opaque members are arranged.

In the present invention, plural substantially tubular opaque members 31, which are highly opaque to radiation, are provided at or near struts constituting the ring pattern units (rings 13) and/or the connecting elements (coiled elements 15). Modes in which the opaque members 31 are provided will be described in detail later. The plural opaque members 31 may be regularly arranged along at least one of the cyclic direction CD, the axis direction LD, and the circumferential direction of the stent.

The opaque members 31 are highly opaque to radiation and thus highly visible when irradiated with radiation. The opaque members 31 may be made of a metal or a synthetic resin. When the stent 11 has the opaque members 31, for example, it is easily visible how the stent 11 is expanded (deployed) or what curved shape is formed throughout the stent 11.

The opaque members 31 are preferably provided at or near substantially non-bendable or non-deformable struts (in coiled elements 15 or rings 13). The substantially non-bendable or non-deformable strut may be the shorter one 15L of the coiled elements 15.

When the opaque members 31 are made of a metal material, examples of the metal material include gold, tantalum, platinum, tungsten, iridium, platinum-tungsten, and any alloys thereof. Alternatively, the opaque members 31 may be made of a radiation-opaque polymer material containing a radiation-opaque filler, for example.

FIGS. 2 and 10 are basically the same developed views, in which FIG. 2 is a developed view showing repeated patterns formed when the stent in the basic form shown in FIG. 1 is virtually developed in a plane, while FIG. 10 is an actual developed view of the stent in the basic form. FIGS. 11 to 16 are actual developed views of stents according to embodiments of the present invention.

FIG. 11 shows a stent 11-1 having a first arrangement pattern. In the stent 11-1, (six) opaque members 31 are provided in a zig-zag manner in the axis direction LD at six places on the leg portions 17a of the rings 13 arranged along the cyclic direction CD. The six opaque members 31 are arranged so as not to interfere with one another when the stent 11-1 is radially compressed (the same applies hereinafter). In the stent 11-1, two second opaque members 32 are each provided at a distal end in a different manner from that of the opaque members 31 (the same applies hereinafter). The six opaque members 31 form two groups each including three members 31. The opaque members 31 and the two second opaque members 32 make it easy to identify what shape the stent has when curved and at what position the distal end of the stent is located (the same applies hereinafter). In the drawings, the opaque members 31 and 32 are each indicated by being enclosed in a dashed line circle (the same applies hereinafter).

FIG. 12 shows a stent 11-2 having a second arrangement pattern. In the stent 11-2, (four) opaque members 31 are provided in a zig-zag manner in the axis direction LD at four places on the leg portions 17a of the rings 13 arranged along the cyclic direction CD. The four opaque members 31 form two groups each including two members 31. The two groups are spaced apart from each other in the axis direction LD.

FIG. 13 shows a stent 11-3 having a third arrangement pattern. In the stent 11-3, (two) opaque members 31 are provided at two places, which are staggered in the axis direction LD, on the leg portions 17a of the rings 13 arranged along the cyclic direction CD.

The overall scaffold of the stents shown in FIGS. 11 to 13 and the overall scaffold of the stents shown in FIGS. 14 to 16 are different in dimensional balance although they are basically the same. FIG. 14 shows a stent 11-4 having a fourth arrangement pattern. In the stent 11-4, (11) opaque members 31 are provided in a zig-zag manner in the axis direction LD at 11 places on the leg portions 17a of the rings 13 arranged along the cyclic direction CD. The 11 opaque members 31 form one group.

FIG. 15 shows a stent 11-5 having a fifth arrangement pattern. In the stent 11-5, (six) opaque members 31 are provided in a zig-zag manner in the axis direction LD at six places on the leg portions 17a of the rings 13 arranged along the cyclic direction CD. The six opaque members 31 form two groups each including three members 31. The two groups are spaced apart from each other in the axis direction LD.

FIG. 16 shows a stent 11-6 having a sixth arrangement pattern. In the stent 11-6, (six) opaque members 31 are provided in a zig-zag manner in the axis direction LD at six places on the leg portions 17a of the rings 13 arranged along the cyclic direction CD. The six opaque members 31 form three groups each including two members 31. The three groups are spaced apart from one another in the axis direction LD.

Although not shown, opaque members 31 may also be arranged in the circumferential direction of the stent.

[Modes in which Opaque Members are Provided]

Figure 17:
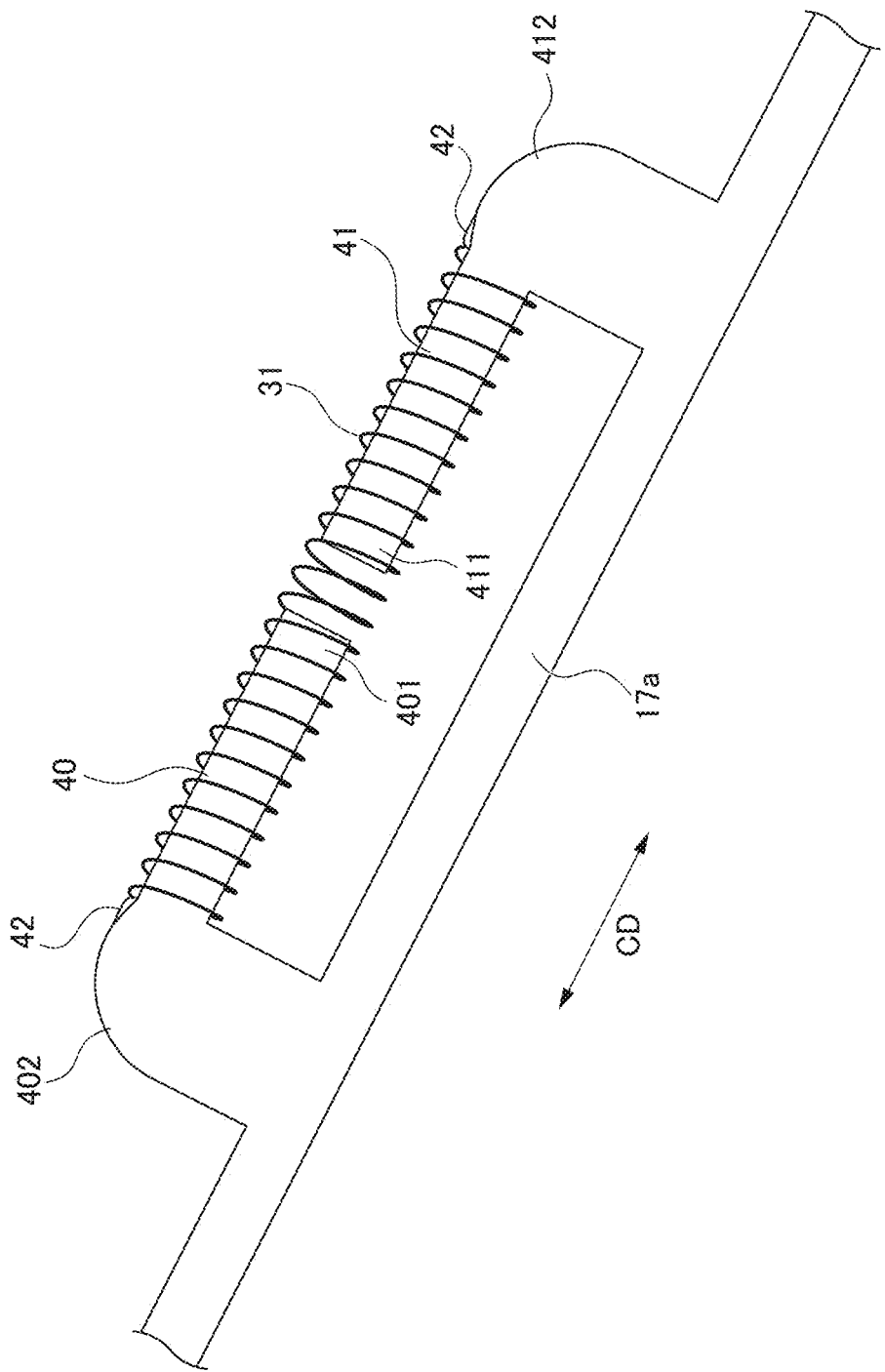
FIG. 17 is a view showing a site where an opaque member is inserted on first and second protrusions.
Figure 18:
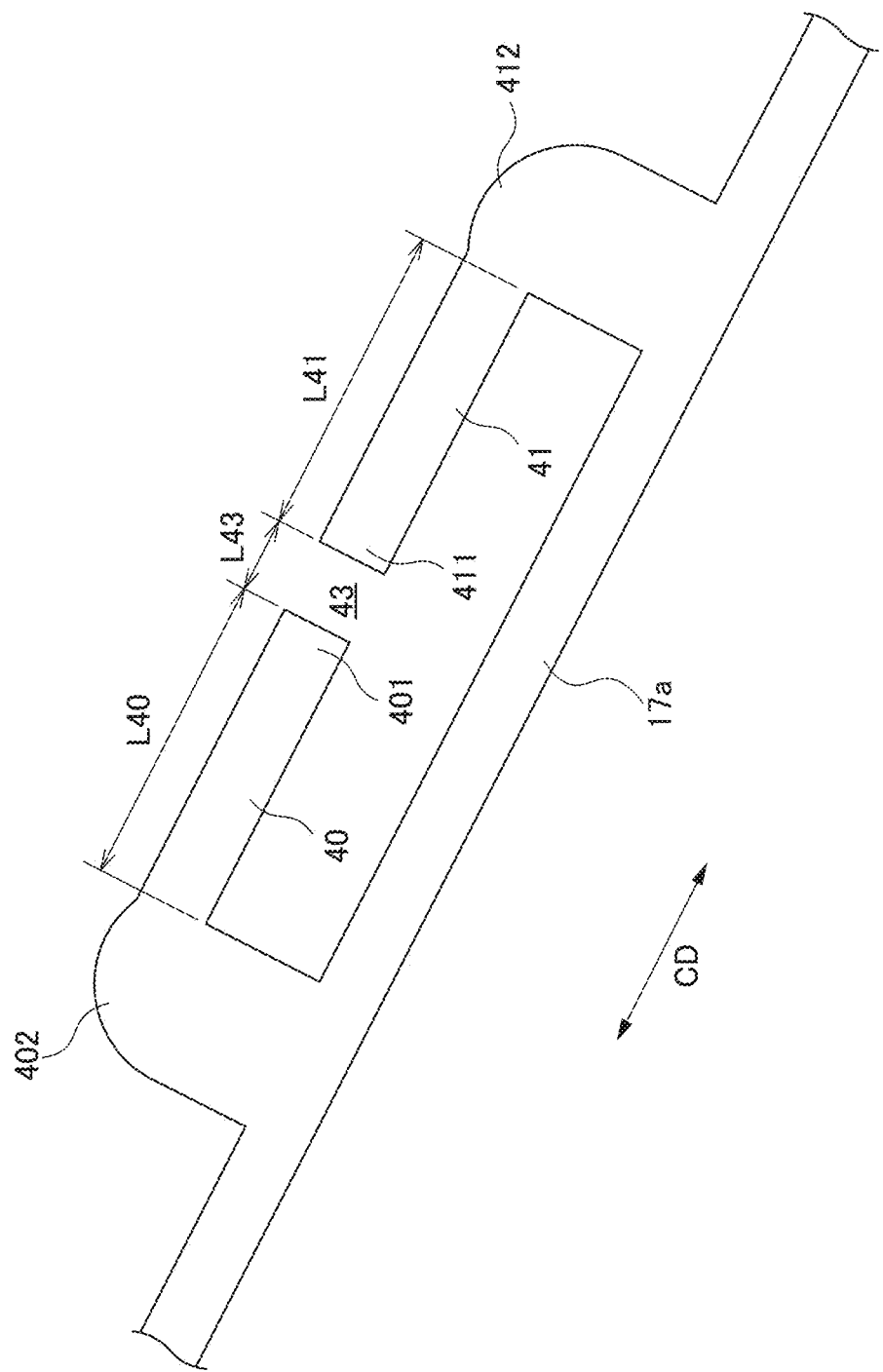
FIG. 18 is a modified view of FIG. 17, showing a structure with no opaque member inserted.

Next, modes in which the opaque members 31 are provided will be described with reference to FIGS. 17 and 18. FIG. 17 is a view showing a site where the opaque member is inserted on first and second protrusions. FIG. 18 is a modified view of FIG. 17, showing a structure with no opaque member inserted.

As shown in FIGS. 17 and 18, paired first and second protrusions 40 and 41 are provided on the leg portion 17a of the ring 13 provided along the cyclic direction CD. The opaque member 31 is fixed on the first and second protrusions 40 and 41 with adhesives 42.

The leg portion 17a of the ring 13 provided along the cyclic direction CD forms a strut extending in a predetermined direction (the cyclic direction CD in this embodiment).

The first protrusion 40 is a substantially L-shaped protrusion that is provided on the leg portion 17a to be located proximal (the left side in FIG. 11) to the second protrusion 41 in the stent 11 and extends in a direction away from the leg portion 17a and in a predetermined direction (cyclic direction CD) toward the distal side (the right side in FIG. 11) of the stent 11. The first protrusion 40 is formed integrally with the leg portion 17a. The portion of the first protrusion 40 extending in the predetermined direction may be longer than the portion of the second protrusion 41 extending in the predetermined direction (L40>L41).

The second protrusion 41 is a substantially L-shaped protrusion that is provided on the leg portion 17a to be located distal to the first protrusion 40 in the stent 11 and extends in a direction away from the leg portion 17a and in a predetermined direction (cyclic direction CD) toward the proximal side of the stent 11. The second protrusion 41 is formed integrally with the leg portion 17a. The first and second protrusions 40 and 41 are spaced in the same direction from the leg portion 17a. The portion of the second protrusion 41 extending in the predetermined direction may be shorter than the portion of the first protrusion 40 extending in the predetermined direction (L41<L40).

The tip 401 of the first protrusion 40 is spaced apart from the tip 411 of the second protrusion 41. The distance L43 between the tips 401 and 411 of the first and second protrusions 40 and 41 is preferably 30 μm to 10 mm. For example, when the stent has an overall length of 10 to 100 mm, the distance L43 may be 30 μm to 300 μm. When the stent has an overall length of 50 to 500 mm, the distance L43 may be 0.5 mm to 5 mm. For example, when the opaque member 31 has an overall length of 100 to 1,000 μm, the distance L43 may be 30 μm to 300 μm. When the opaque member 31 has an overall length of 1 to 10 mm, the distance L43 may be 0.5 mm to 5 mm. There may also be substantially no distance L43 (zero).

The portion of the first protrusion 40 extending in the predetermined direction preferably has a length L40 of 30 μm to 10 mm. For example, when the stent has an overall length of 10 to 100 mm, the length L40 may be 50 to 1,000 μm. When the stent has an overall length of 50 to 500 mm, the length L40 may be 0.5 to 10 mm. For example, when the opaque member 31 has an overall length of 100 to 1,000 μm, the length L40 may be 30 μm to 200 μm. When the opaque member 31 has an overall length of 1 to 10 mm, the length L40 may be 5 mm to 10 mm.

The portion of the second protrusion 41 extending in the predetermined direction preferably has a length L41 of 20 μm to 10 mm. For example, when the stent has an overall length of 10 to 100 mm, the length L41 may be 50 to 1,000 μm. When the stent has an overall length of 50 to 500 mm, the length L41 may be 0.5 to 10 mm. For example, when the opaque member 31 has an overall length of 100 to 1,000 μm, the length L41 may be 30 μm to 200 μm. When the opaque member 31 has an overall length of 1 to 10 mm, the length L41 may be 5 mm to 10 mm.

The first and second protrusions 40 and 41 respectively have convex portions 402 and 412 at the base ends of the portions extending in the predetermined direction, which are on the sides opposite to the leg portion 17a.

The strut provided with the first and second protrusions 40 and 41 is shifted from the adjacent strut in a direction away from the side where the first and second protrusions 40 and 41 are provided. Therefore, the first and second protrusions 40 and 41 can be provided such that the distance over which the first and second protrusions 40 and 41 protrude is lower than the reference level along the longitudinal direction throughout the strut.

The opaque member 31 is a highly radiation-opaque, substantially tubular member having both end portions in which the first and second protrusions 40 and 41 are inserted. The term "substantially tubular" has a broad meaning including not only a completely tubular shape but also any shape that can be considered a tube when viewed as a whole. Examples of the substantially tubular shape include coil spring (spiral) shapes and shapes with a C-shaped cross-section. The opaque member 31 is preferably stretchable in the axial (longitudinal) direction of the tube as manufactured. In the present embodiment, the opaque member 31 is a coil spring. Preferably, the opaque member 31 with such features locally has a sparse area with a spacing ratio higher than a predetermined spacing ratio. This feature allows the opaque member 31 to compress during manufacture, so that the opaque member 31 can be easily inserted on the first and second protrusions 40 and 41, and can be a not-excessively-firm coil spring.

To ensure the visibility, the opaque member 31 preferably has an outer diameter of 0.2 mm or more. For example, the opaque member 31 should have an outer diameter of 0.52 mm or less in order to be inserted into a catheter with an inner diameter of 0.027 inches, and should have an outer diameter of 0.55 mm or less in order to be inserted into a catheter with an inner diameter of 0.028 inches.

The adhesive 42 may be a suitable resin-based adhesive such as a UV-curable adhesive, a thermosetting adhesive, a two-component adhesive, or a cyanoacrylate-based adhesive. The term "adhesive" should be broadly interpreted to also include metallic adhesives such as solder and brazing materials.

Figure 19A:
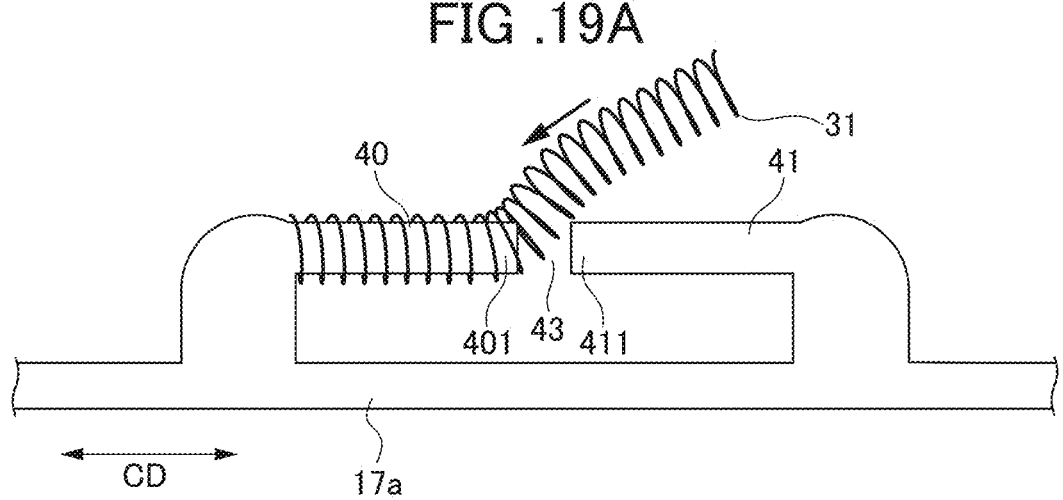
FIG. 19A is a diagram showing a process of inserting an opaque member sequentially onto first and second protrusions.
Figure 19B:
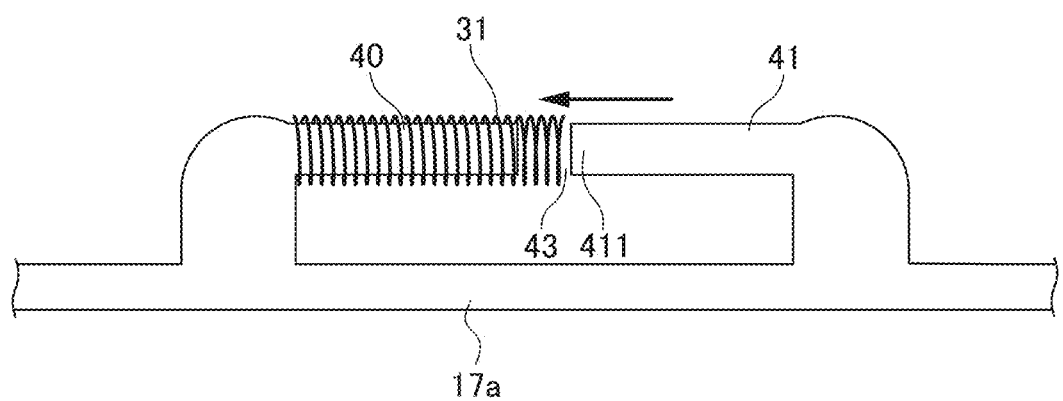
FIG. 19B is a diagram showing a process of inserting an opaque member sequentially onto first and second protrusions.
Figure 19C:
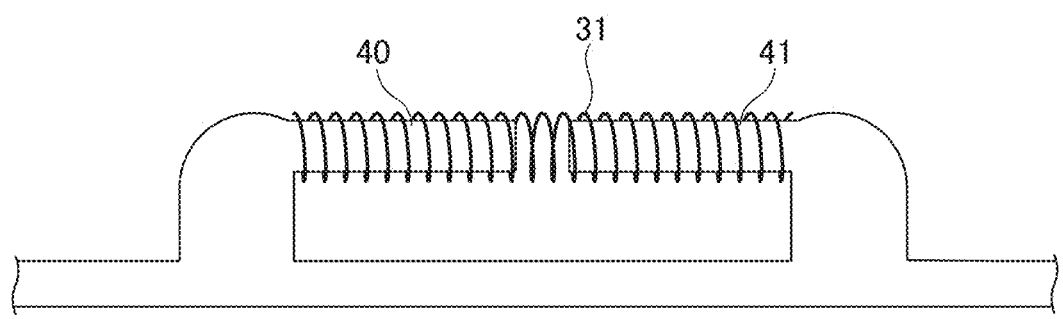
FIG. 19C is a diagram showing a process of inserting an opaque member sequentially onto first and second protrusions.

FIGS. 19A to 19C are diagrams illustrating a process of inserting the opaque member sequentially onto the first and second protrusions. As shown in FIG. 19A, one end portion of the opaque member 31 consisting of a coil spring is inserted onto the first protrusion 40. As shown in FIG. 19B, the opaque member 31 strikes a portion close to the base end of the first protrusion 40 and then compresses. Therefore, the other end of the opaque member 31 is located at or near the spacing 43 between the tips 401 and 411 of the first and second protrusions 40 and 41. As shown in FIG. 19C, the other end of the opaque member 31 is then inserted onto the second protrusion 41. By taking advantage of the elastic restoring force of the opaque member 31, the other end of the opaque member 31 can be easily inserted onto the second protrusion 41. It should be noted that the insertion process shown in FIGS. 19A to 19C is an example and the insertion process (how to insert) varies with, for example, the length or stretchability of the opaque member 31, the length of the first protrusion 40 and/or the second protrusion 41, and the distance L43 between the tips 401 and 411 of the first and second protrusions 40 and 41. Even in different insertion processes, the distance L43 makes it easy to insert the opaque member 31 onto the first and second protrusions 40 and 41 as compared to substantially no distance.

Figure 20A:
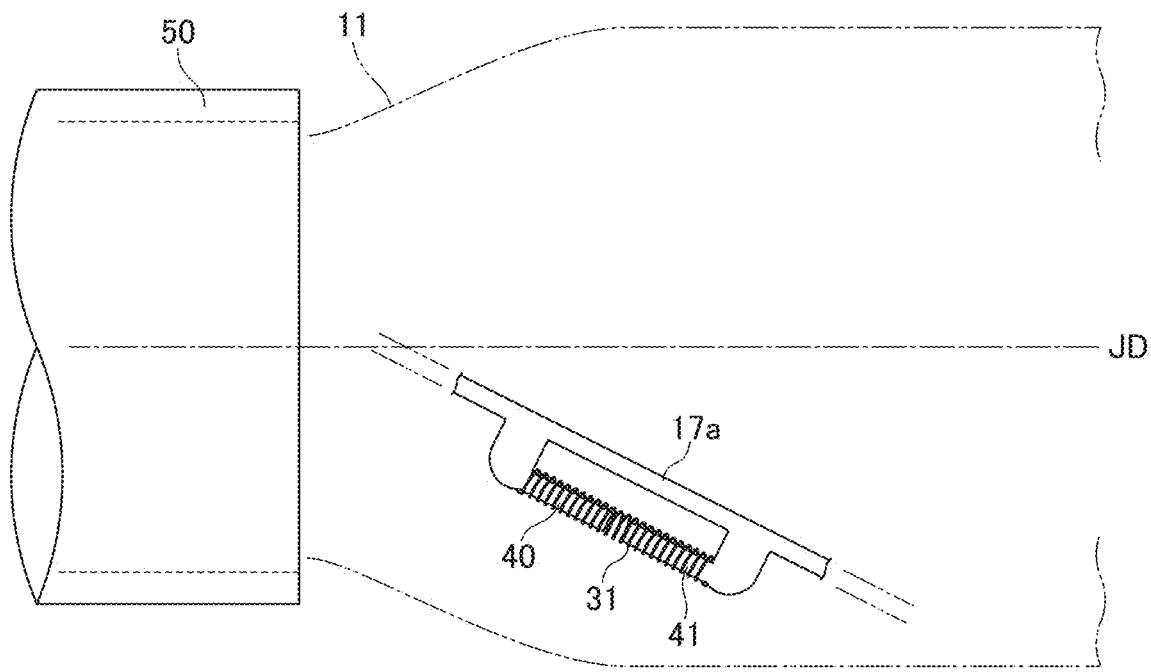
FIG. 20A is a schematic diagram showing how a portion including an opaque member enters a catheter.
Figure 20B:
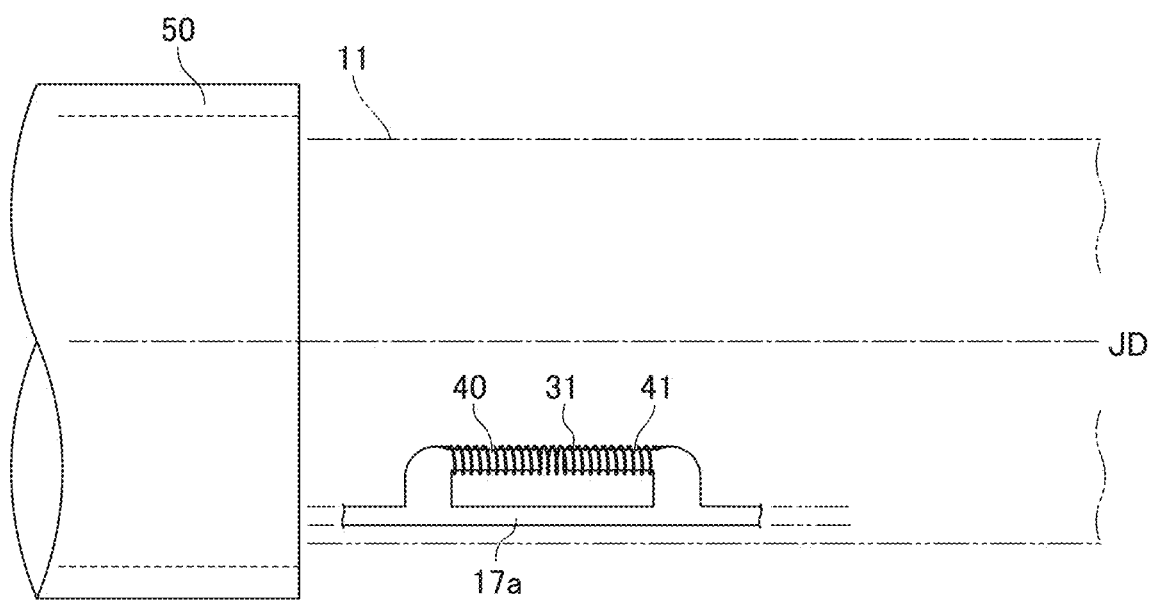
FIG. 20B is a schematic diagram showing how a portion including an opaque member enters a catheter.

FIGS. 20A and 20B are diagrams showing how a portion including the opaque member enters a catheter. In a process of inserting the stent into a catheter 50, the portions of the first and second protrusions 40 and 41 extending in the predetermined direction are placed along the direction JD in which the stent is inserted into the catheter 50 and placed inside the leg portion 17a in the radial direction of the catheter 50. Specifically, the first and second protrusions 40 and 41 can behave as follows. As shown in FIG. 20A, at a position far from the opening of the catheter 50, the first and second protrusions 40 and 41 may be placed outside the leg portion 17*a* in the radial direction of the catheter 50, and/or the direction in which the strut provided with the first and second protrusions 40 and 41 extends may be inclined to the insertion direction JD. In the insertion process, however, as shown in FIG. 20B, the direction in which the strut provided with the first and second protrusions 40 and 41 extends is aligned substantially in parallel to the insertion direction JD, and the first and second protrusions 40 and 41 are placed inside the leg portion 17*a* in the radial direction of the catheter 50.

Figure 21:
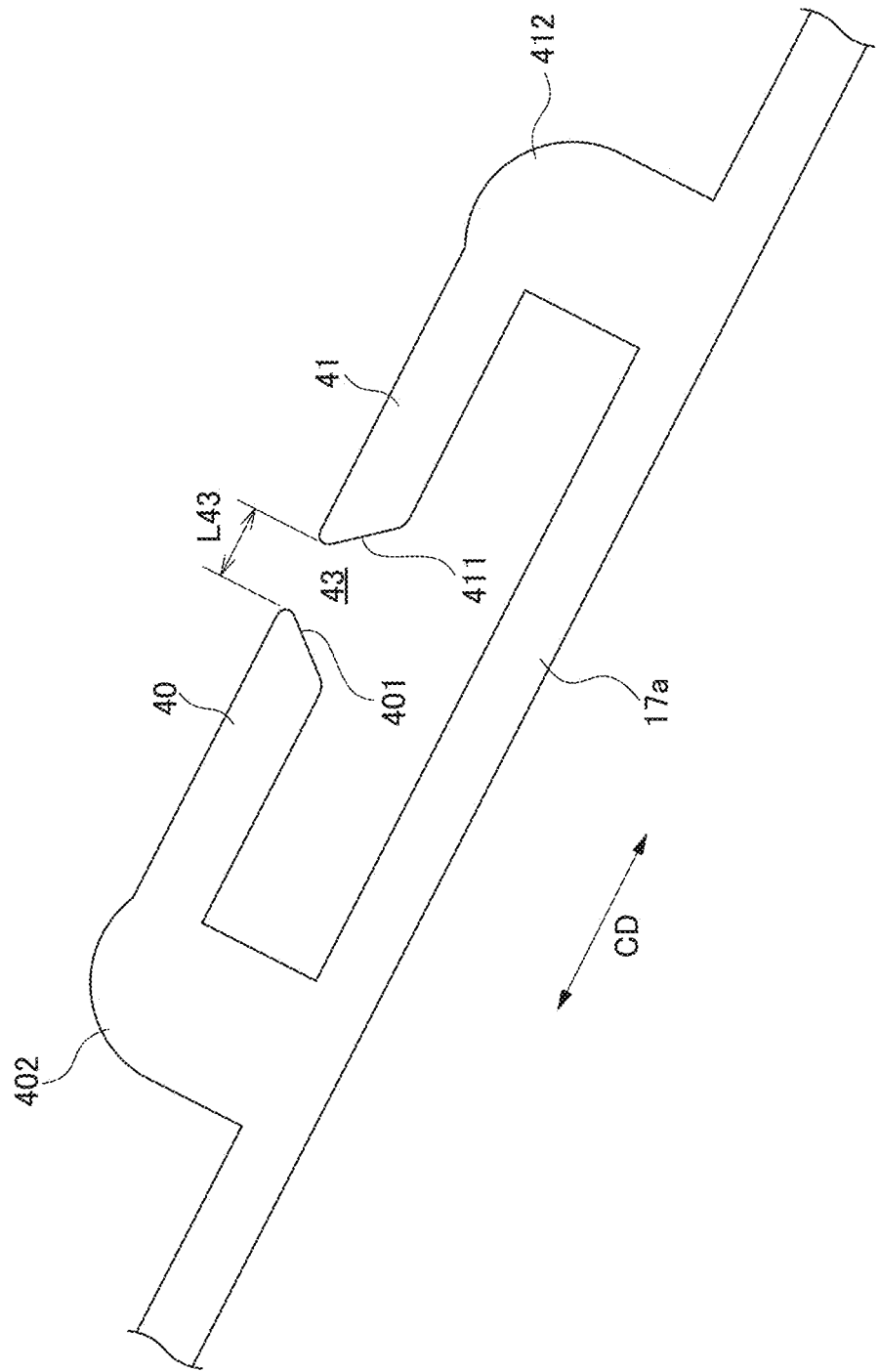
FIG. 21 is a view showing modifications of first and second protrusions, which corresponds to FIG. 18.

FIG. 21 is a view showing modifications of the first and second protrusions, which corresponds to FIG. 18. In a modified example shown in FIG. 21, a pair of first and second protrusions 40 and 41 are provided having tips facing and spaced apart from each other with a distance L43 (spacing 43) between them. The first and second protrusions 40 and 41 each have a tip portion with an inclined shape on a side facing the leg portion 17*a*.

Advantageous Effects of Embodiments

The stents according to embodiments of the present invention bring about advantageous effects as described below. As shown in FIGS. 17 and 18, a stent according to an embodiment of the present invention includes: a strut extending in a predetermined direction; a first protrusion 40 provided on the strut, the first protrusion 40 being substantially L-shaped and extending in a direction away from the strut and in a direction toward a distal side in the predetermined direction; a second protrusion 41 that is provided on the strut and located distal to the first protrusion, the second protrusion 41 being substantially L-shaped, extending in a direction away from the strut and in a direction toward a proximal side in the predetermined direction, and having a tip 411 spaced apart from a tip 401 of the first protrusion 40; and an opaque member 31 being substantially tubular and highly opaque to radiation, the opaque member 31 having two end portions in which the first and second protrusions 40 and 41 are inserted, respectively. Such a stent has a structure in which the opaque member 31 is supported from both sides, which increases the structural strength and prevents the ends of the opaque member 31 from projecting outside. Furthermore, such a stent has high reliability to prevent the opaque member 31 from coming off in a luminal structure. In particular, the opaque member 31 is effectively prevented from coming off when the stent is inserted into a blood vessel with many bent portions. The tips 401 and 411 of the first and second protrusions 40 and 41 are spaced apart from each other. Taking advantage of the spacing 43 between the tips 401 and 411 of the first and second protrusions 40 and 41, for example, the opaque member 31 can be attached as shown in FIGS. 19A to 19C to the strut. Therefore, the stent has a high level of ease of attachment with respect to the attachment of the opaque member 31 to the strut. When the stent is for use in cerebral blood vessels, the opaque member 31 should be thin and small. In such a case, the high level of ease of attachment is particularly advantageous.

The opaque member 31 being substantially tubular may be stretchable in the tube axis direction. According to the stent with such a feature, the opaque member 31 can be compressed in the axis direction and inserted through the spacing 43 between the tips 401 and 411 of the first and second protrusions 40 and 41, so that both end portions of the opaque member 31 can be easily inserted onto the first and second protrusions 40 and 41.

As shown in FIG. 18, the portion of the first protrusion 40 extending in the predetermined direction may be longer than the portion of the second protrusion 41 extending in the predetermined direction. The stent with such a feature can further prevent the opaque member 31 from coming off when the stent is moved toward the proximal side of a catheter. Moreover, when the insertion process shown in FIGS. 19A to 19C is used, the opaque member 31 can be compressed as much as possible on the first protrusion 40, which is longer than the second protrusion 41, so that the other end of the opaque member 31 can be easily positioned at or near the spacing 43 between the tips 401 and 411 of the first and second protrusions 40 and 41.

As shown in FIG. 21, the first and second protrusions 40 and 41 may each have a tip portion with an inclined shape on a side facing the strut. In the manufacture of the stent with such a feature, the opaque member 31 can be easily inserted onto the first and second protrusions 40 and 41, so that the stent can be easily manufactured.

As shown in FIG. 18, the first and second protrusions 40 and 41 may each have a convex-shaped portion 402 (412) that is opposite to the strut and at a base end of a portion extending in the predetermined direction. In the stent with such a feature, the adhesive 42 does not cause a significant difference in level on the strut, so that, during use, the stent is less likely to damage the inside of blood vessels.

As shown in FIGS. 20A and 20B, the first and second protrusions 40 and 41 may have portions that extend in the predetermined direction and are configured to be placed along a direction in which the stent is inserted into a catheter 50 in a process of inserting the stent into the catheter 50 and configured to be placed inside the strut in the radial direction of the catheter 50 in the process of inserting the stent into the catheter 50. In the process of inserting the stent with such features into the catheter 50, the opaque member 31 inserted on the first and second protrusions 40 and 41 is less likely to come into contact with the catheter 50. Therefore, the stent has a high level of ease of insertion into the catheter 50.

Preferred embodiments of the present invention have been described above. It will be understood that the embodiments described above are not intended to limit the present invention and may be implemented in various ways.

EXPLANATION OF REFERENCE NUMERALS

11: Stent
17*a*: Leg portion (strut)
31: Opaque member
40: First protrusion
41: Second protrusion
50: Catheter

What is claimed is:

1. A substantially cylindrical stent comprising:
   a strut extending in a predetermined direction;
   a first protrusion provided on the strut, the first protrusion being substantially L-shaped and extending in a direction away from the strut and in a direction toward a distal side in the predetermined direction;
   a second protrusion that is provided on the strut and located distal to the first protrusion, the second protrusion being substantially L-shaped, extending in a direction away from the strut and in a direction toward a proximal side in the predetermined direction, and having a tip spaced apart from a tip of the first protrusion; and an opaque member being substantially tubular and highly opaque to radiation, the opaque member having two end portions in which the first and second protrusions are inserted, respectively.

2. The substantially cylindrical stent according to claim 1, wherein a distance of 30 μm to 10 mm is provided between the tip of the first protrusion and the tip of the second protrusion.

3. The substantially cylindrical stent according to claim 1, wherein the opaque member being substantially tubular is stretchable in a tube axis direction.

4. The substantially cylindrical stent according to claim 1, wherein the first protrusion has a portion that extends in the predetermined direction and is longer than a portion of the second protrusion extending in the predetermined direction.

5. The substantially cylindrical stent according to claim 1, wherein the first and second protrusions each have a tip portion with an inclined shape on a side facing the strut.

6. The substantially cylindrical stent according to claim 1, wherein the first and second protrusions each has a convex-shaped portion that is opposite to the strut and at a base end of a portion extending in the predetermined direction.

7. The substantially cylindrical stent according to claim 1, wherein the first and second protrusions have portions that extend in the predetermined direction and are configured to be placed along a direction in which the stent is inserted into a catheter in a process of inserting the stent into the catheter, and configured to be placed inside the strut in a radial direction of the catheter in the process of inserting the stent into the catheter.

* * * * *